US006562798B1

(12) United States Patent
Schwartz

(10) Patent No.: US 6,562,798 B1
(45) Date of Patent: May 13, 2003

(54) IMMUNOSTIMULATORY OLIGONUCLEOTIDES WITH MODIFIED BASES AND METHODS OF USE THEREOF

(75) Inventor: David Schwartz, Encinitas, CA (US)

(73) Assignee: Dynavax Technologies Corp., Berkeley, CA (US)

( * ) Notice: Subject to any disclaimer, the term of this patent is extended or adjusted under 35 U.S.C. 154(b) by 0 days.

(21) Appl. No.: 09/324,191

(22) Filed: Jun. 1, 1999

Related U.S. Application Data

(60) Provisional application No. 60/088,310, filed on Jun. 5, 1998.

(51) Int. Cl.[7] .......................... A01N 43/04; C12Q 1/68; C12P 19/34; C12N 5/00; C07H 21/02

(52) U.S. Cl. ........................ 514/44; 435/6; 435/91.1; 435/375; 435/455; 536/23.1

(58) Field of Search ................... 424/85.1, 450, 424/1.21, 1.53, 1.57, 452; 435/89, 6, 91.9, 91.5, 91.51, 69.2, 325, 375, 455, 70.1, 69.7, 69.3, 91.31; 530/395, 300, 351, 325; 536/24.5, 25.3; 514/44, 49, 53, 54, 588

(56) References Cited

U.S. PATENT DOCUMENTS

| | | | |
|---|---|---|---|
| 4,948,882 A | | 8/1990 | Ruth |
| 5,780,448 A | * | 7/1998 | Davis et al. .................. 514/44 |
| 5,968,909 A | * | 10/1999 | Agrawal et al. .............. 514/44 |
| 6,194,388 B1 | | 2/2001 | Krieg et al. |
| 6,207,646 B1 | | 3/2001 | Krieg et al. |
| 6,214,806 B1 | | 4/2001 | Krieg et al. |
| 6,218,371 B1 | | 4/2001 | Krieg et al. |

FOREIGN PATENT DOCUMENTS

| | | |
|---|---|---|
| WO | WO 89/09779 A1 | 10/1989 |
| WO | WO 89/09779 | 10/1989 |
| WO | 9816247 | * 10/1997 |
| WO | WO 98/55495 | 12/1998 |
| WO | WO 98/55495 A2 A3 | 12/1998 |

OTHER PUBLICATIONS

Branch, A. 1998 Trends in Bioch. Sci (CTIBS) vol. 23: pp. 45–50.*
Crooke, S. 1998. Anti Search Res. and Application. Chapter 1, PP 1–50. (Publ. Seringer).*
Kuramato, E, et al (1992) Jpn. J. Cancer Res. vol. 83, pp. 1128–1131.*
Sanghui, Y.S. (1993) Chapter 15 from Antisense Res. and Applications. pp. 273–285. CRC Press.*
Uhlmann, E et al (1990) Chemical Reviews. vol. 90, pp. 544–579.*
Boggs, R. T. et al. (1997). "Characterization and Modulation of Immune Stimulation by Modified Oligonucleotides," *Antisense & Nucleic Acid Drug Development* 7:461–471.

Brennan, C. A. et al. (1986). "The Effects of Base Analogue Substitutions on the Methylation by the EcoRI Modification Methylase of Octadeoxyribonucleotides Containing Modified EcoRI Recognition Sequences," *J. Biol. Chem.* 261(16):7279–7286.
Dutta, R. et al. (1998). "Binding of the Modified Daunorubicin WP401 Adjacent to a T–G Base Pair Induces the Reverse Watson–Crick Conformation: Crystal Structures of the WP401–TGGCCG and WP401–CGG[br$^5$C]CG Complexes," *Nucleic Acids Res.* 26(12):3001–3005.
Ferrer, E. et al. (1997). "Preparation and Properties of Oligodeoxynucleotides Containing 5–Iodouracil and 5–Bromo–5–Iodocytosine," *Bioconjugate Chem.* 8(5):757–761.
Goddard, A. J. et al. (1988). "Synthesis of a Phosphoramidite of 2'–deoxy–5,6–dihydro–5–azacytidine. Its Potential Application in the Synthesis of DNA Containing Dihydro–5–aza and 5–azacytosine Bases," *Tetrahedron Lett.* 29(15): 1767–1770.
Hardin, C. C. et al. (1988). "Characterization of Anti–Z–RNA Polyclonal Antibodies: Epitope Properties and Rectognition of Z–DNA," *Biochemistry* 27(11):4169–4177.
Jean, Y. C. et al. (1993). "Z–DNA Structure of a Modified DNA Hexamer at 1.4–Å Resolution: Aminohexyl–5'–d(pCpGp[Br$^5$C]pGpCpG)," *Biochemistry* 32(1):381–388.
Krieg, A. M. et al. (1995). "CPG Motifs in Bacterial DNA Trigger Direct B–cell Activation," *Nature* 374:546–549.
Nguyen, H. et al. (1997). "Studies Towards the Design of a Modified GC Base Pair With Stability Similar to That of the AT Base Pair," *Tetrahedron Letters* 38(23):4083–4086.
Theriault, N. Y. et al. (1988). "Studies on the Base Pair Binding Specificity of CC–1065 to Oligomer Duplexes," *Chem. Biol. Interact.* 65(2):187–201.
Tokunaga, T. et al. (1999). "How BCG Led to the Discovery of Immunostimulatory DNA," *Jpn. J. Infect. Dis.* 52:1–11.
Yoon, C. et al. (1988). "Structure of an Alternating–B DNA Helix and its Relationship of A–tract DNA," *Proc. Natl. Acad. Sci. USA* 85(17):6332–6336.
Sanghvi, Y. S. et al. (1993), "Antisense Oligodeoxynucleotides: Synthesis, Biophysical and Biological Evaluation of Oligodeoxynucleotides Containing Modified Pyrimidines," *Nucl. Acids Res.* 21(14):3197–3203.

(List continued on next page.)

Primary Examiner—Sean McGarry
Assistant Examiner—Jane Zara
(74) Attorney, Agent, or Firm—Morrison & Foerster LLP

(57) ABSTRACT

Immunomodulatory oligonucleotide compositions are disclosed. These oligonucleotides comprise an immunostimulatory hexanucleotide sequence comprising a modified cytosine. These oligonucleotides can be administered in conjunction with an immunomodulatory peptide or antigen. Methods of modulating an immune response upon administration of the oligonucleotide comprising a modified immunostimulatory sequence are also disclosed.

67 Claims, 4 Drawing Sheets

OTHER PUBLICATIONS

Zarling, D. A. et al. (1984). "Immunoglobulin Recognition of Synthetic and Natural Left–Handed Z DNA Conformations and Sequences," *J. Mol. Biol.* 176:369–415.

Agrawal et al., "Efficient methods for attaching non–radioactive labels to the 5' ends of synthetic oligodeoxyribonucleotides" (1986) *Nucleic Acids Res.* 14:6227–6245.

*Animal Cell Culture: A Practical Approach,* (1987) R.I. Freshney, ed., IRL Press, Oxford, (Table of Contents).

Aramaki et al., "Interferon –γ inductive effect of liposomes as an immunoadjuvant" (1995) *Vaccine* 13:1809–1814.

Atherton et al., "Synthesis of a 21–residue fragment of human proinsulin by the polyamide solid phase method" (1981) *Hoppe–Seylers Z. Physiol. Chem.* 362:833–839.

Ballas et al., "Induction of NK activity in murine and human cells by CpG motifs in oligodeoxynucleotides and bacterial DNA" (1996) *J. Immunol.* 157:1840–1845.

Benoit et al., "Peptides. Strategies for antibody production and radioimmunoassay" (1987) *Neuromethods* 6:43–72.

Bischoff et al., "Introduction of 5'–terminal functional groups into synthetic oligonucleotides for selective immobilization" (1987) *Analytical Biochemistry* 164:336–344.

Blanks et al., "An oligodeoxynucleotide affinity column for the isolation of sequence specific DNA binding proteins" (1988) *Nucleic Acids Res.* 16:10283–10299.

Bliss et al., "IL–12, as an adjuvant, promotes a T helper 1 cell, but does not suppress a T helper 2 cell recall response" (1996) *J. Immunol.* 156:887–894.

Boujrad et al., "Inhibition of hormone–stimulated steroidogenesis in cultured Leydig tumor cells by a cholesterol–linked phosphorothioate oligodeoxynucleotide antisense to diazepam–binding inhibitor" (1993) *Proc. Natl. Acad. Sci. USA* 90:5728–2731.

Bradley et al., "Hepatitis A virus: Growth characteristics of in vivo and in vitro propagated wild and attenuated virus strains" (1984) *J. Med. Virol.* 14:373–386.

Braun et al., "Immunogenic duplex nucleic acids are nuclease resistant" (1988) *J. Immunol.* 141:2084–2089.

Breiteneder et al., "The gene coding for the major birch pollen allergen Betvl, is highly homologous to a pea disease resistance response gene" (1989) *EMBO J.* 8:1935–1938.

Broide et al., "Intradermal gene vaccination down–regulates both arms of the allergic response" (1997) *J. Allergy Clin. Immunol.* 99:Abstracts–S129: 523.

Chaturvedi et al., "Stabilization of triple–stranded oligonucleotide complexes: use of probes containing alternating phosphodiester and stereo–uniform cationic phosphoramidate linkages" (1996) *Nucleic Acids Res.* 24:2318–2323.

Chua et al., "Sequence analysis of cDNA coding for a major house dust mite allergen, Der p 1" (1988) *J. Exp. Med.* 167:175–182.

Chua et al., "Expression of *Dermatophagoides pteronyssinus* allergen, Der p II, in *Escherichia coli* and the binding studies with human IgE" (1990) *Int. Arch. Allergy Appl. Immunol.* 91:124–129.

Connolly, Bernard A., "Chemical synthesis of oligonucleotides containing a free sulphydryl group and subsequent attachment of thiol specific probes" (1985) *Nucleic Acids Res.* 13:4485–4502.

Connolly, Bernard A., "The synthesis of oligonucleotides containing a primary amino group at the 5'–terminus" (1987) *Nucleic Acids Res.* 15:3131–3139.

Corey et al., "Generation of a hybrid sequence–specific single–stranded deoxyribonuclease" (1987) *Science* 238:1401–1403.

Cowdery et al., "Bacterial DNA induces NK cells to produce IFN–γ in vivo and increases the toxicity of lipopolysaccharides" (1996) *J. Immunol.* 156:4570–4575.

*Current Communications in Molecular Biology,* (1987) "Gene transfer vectors for mammalian cells" Jeffrey H. Miller, Michele P. Calos, eds., Cold Spring Harbor Laboratory (Table of Contents).

*Current Protocols in Immunology,* (1998) John E. Coligan et al., eds., John Wiley & Sons, Inc., (Table of Contents).

*Current Protocols in Molecular Biology,* (1995) Frederick M. Ausubel et al., eds., John Wiley & Sons, Inc., (Table of Contents).

Dixon, B., "The third vaccine revolution" (1995) *Bio/Technology* 13:420–421.

Elsayed et al., "The structural requirements of epitopes with IgE binding capacity demonstrated by three major allergens from fish, egg and tree pollen" (1991) *Scand. J. Clin. Lab. Invest. Suppl.* 204:17–31.

*Enzymatic Peptide Synthesis,* Willi Kullman, ed., CRC Press, Inc., (Table of Contents).

Gao et al., "Circularization of oligonucleotides by disulfide bridge formation" (1995) *Nucleic Acids Res.* 23:2025–2029.

Geoghegan et al., "Site–directed conjugation of nonpeptide groups to peptides and proteins via periodate oxidation of a 2–amino alcohol. Application to modification at N–terminal serine" (1992) *Bioconjug. Chem.* 3:138–146.

Goodchild, John, "Conjugates of oligonucleotides and modified oligonucleotides: A review of their synthesis and properties" (1990) *Bioconjug. Chem.* 1:165–187.

Grabarek et al., "Zero–length crosslinking procedure with the use of active esters" (1990) *Anal. Biochem.* 185:131–135.

Halpern et al., "Bacterial DNA induces murine interferon–γ production by stimulation of interleukin–12 and tumor necrosis factor–α" (1996) *Cell. Immunol.* 167:72–78.

*Handbook of Experimental Immunology,* "Vol. 4: Applications of immunological methods in biomedical sciences", D. M. Weir, ed., Blackwell Scientific Publications, Oxford (Table of Contents).

Haralambidis et al., "The preparation of polyamide–oligonucleotide probes containing multiple non–radioactive labels" (1990) *Nucleic Acids Res.* 18:501–505.

Haralambidis et al., "The synthesis of polyamide–oligonucleotide conjugate molecules" (1990) *Nucleic Acids Res.* 18:493–499.

Jäger et al., "Oligonucleotide N–alkylphosphoramidates: Synthesis and binding to polynucleotides" (1988) *Biochem.* 27:7237–7246.

James et al., "Safe adminstration of the meales vaccine to children allergic to eggs" (1995) *N. Engl. J. Med.* 332:1262–1266.

Jiang et al., "Inactivation of poliovirus with β–propiolactone" (1986) *J. Biol. Stand.* 14:103–109.

Kessler, Christoph, "Nonradioactive labeling methods for nucleic acids" (1992) *Nonisotopic DNA Probe Techniques,* Kricka (ed.), Academic Press, Inc., pp. 29–92.

Klinman et al., "CpG motifs present in bacterial DNA rapidly induce lymphocytes to secrete interleukin 6, interleukin 12, and interferon γ" (1996) *Proc. Natl. Acad. Sci. USA* 93:2879–2883.

Kremsky et al., "Immobilization of DNA via oligonucleotides containing an aldehyde or carboxylic acid group at the 5' terminus" (1987) *Nucleic Acids Res.* 15:2891–2909.

Krieg et al., "CpG motifs in bacterial DNA trigger direct B–cell activation" (1995) *Nature* 374:546–549.

Kuramoto et al., "In situ infiltration of natural killer–like cells induced by intradermal injection of the nucleic acid fraction from BCG" (1989) *Microbiol. Immunol.* 33:929–940.

Latimer et al., "Specificity of monoclonal antibodies produced against phosphorothioate and ribo modified DNAs" (1995) *Mol. Immunol.* 32:1057–1064.

Lea et al., "Cloning and sequencing of cDNAs encoding the human sperm protein, Sp17" (1996) *Biochim. Biophys. Acta* 1307:263–266.

Leff, David N., "Non–lipid polymer beats liposome vector in mouse gene therapy experiment" (1997) *Bioworld* 86:1–2.

*Liposomes: From Physics to Applications,* (1993) D.D. Lasic, Elsevier, Amsterdam, (Table of Contents).

Malley, Arthur, "The immune response of offspring mice from mothers immunized during pregnancy with protein antigens" (1989) *J. Reprod. Immunol.* 16:173–186.

Manickan et al., "Genetic immunization against herpes simplex virus" (1995) *J. Immunol.* 155:259–265.

Messina et al., "The influence of DNA structure on the in vitro stimulation of murine lymphocytes by natural and synthetic polynucleotide antigens" (1993) *Cell. Immunol.* 147:148–157.

Miller et al., "Syntheses and properties of adenine and thymine nucleoside alkyl phosphotriesters, the neutral analogs of dinucleoside monophosphates" (1971) *JACS* 93:6657–6665.

Mitragotri et al., "Ultrasound–mediated transdermal protein delivery" (1995) *Science* 269:850–853.

*Molecular Cloning: A Laboratory Manual.* (1989) Second Edition, J. Sambrook et al., eds., Cold Spring Harbor Laboratory Press, (Table of Contents).

Nelson et al., "Bifunctional oligonucleotide probes synthesized using a novel CPG support are able to detect single base pair mutations" (1989) *Nucleic Acids Res.* 17:1787–1794.

*Oligonucleotide Synthesis. A Practical Approach,* (1984) M.J. Gait, ed., IRL Press, (Table of Contents).

O'Shannessy et al., "Specific conjugation reactions of the oligosaccharide moieties of immunoglobulins" (1985) *J. Applied Biochem.* 7:347–355.

Pardoll et al., "Exposing the immunology of naked DNA vaccines" (1995) *Immunity* 3:165–169.

Pertmer et al., "Influenza virus nucleoprotein–specific immunoglobulin G subclass and cytokine responses elicited by DNA vaccination are dependent on the route of vector DNA delivery" (1996) *J. Virol.* 70:6119–6125.

Peyrottes et al., "Oligodeoxynucleoside phosphoramidates (P–NH$_2$): synthesis and thermal stability of duplexes with DNA and RNA targets" (1996) *Nucleic Acids Res.* 24:1841–1848.

Pisetsky, David S., "The immunologic properties of DNA" (1996) *J. Immunol.* 156:421–423.

Rafnar et al., "Cloning of Amb a I (antigen E), the major allergen family of short ragweed pollen" (1991) *J. Biol. Chem.* 266:1229–1236.

Raz et al., "Intradermal gene immunization: The possible role of DNA uptake in the induction of cellular immunity to viruses" (1994) *Proc. Natl. Acad. Sci. USA* 91:9519–9523.

Raz et al., "Preferential induction of a Th$_1$ immune response and inhibition of specific IgE antibody formation by plasmid DNA immunization" (1996) *Proc. Natl. Acad. Sci. USA* 93:5141–5145.

Rogers et al., "Recombinant Fel d I: Expression, purification, IgE binding and reaction with cat–allergic human T cells" (1993) *Mol. Immunol.* 30:559–568.

Roget et al., "Synthesis and use of labelled nucleoside phosphoramidite building blocks bearing a reporter group: biotinyl, dinitrophenyl, pyrenyl and dansyl" (1989) *Nucleic Acids Res.* 17:7643–7651.

Ruth, Jerry L., "Chemical synthesis of non–radioactively–labeled DNA hybridization probes" *Fourth Annual Congress for Recombinant DNA Research,* p. 123.

Ruth, Jerry L., "Oligodeoxynucleotides with reporter groups attached to the base" (1991) *Oligonucleotides and Analogues: A Practical Approach,* Eckstein, ed., IRL Press, pp. 255–282.

Sato et al., "Immunostimulatory DNA sequences necessary for effective intradermal gene immunization" (1996) *Science* 273:352–354.

Schultz et al., "Oligo–2'–fluoro–2'–deoxynucleotide N3'→P5' phosphoramidates: synthesis and properties" (1996) *Nucleic Acids Res.* 24:2966–2973.

*Selected Methods in Cellular Immunology,* Mishell B.B. et al., eds., W. H. Freeman & Co., San Francisco (Table of Contents).

Shimada et al., "In vivo augmentation of natural killer cell activity with a deoxyribonucleic acid fraction of BCG" (1986) *Jpn. J. Cancer Res.* 77:808–816.

Sinha et al., "Oligonucleotides with reporter groups attached to the 5'–terminus" (1991) *Oligonucleotide Analogues: A Practical Approach,* Eckstein, ed., IRL Press, pp. 185–210.

Staros et al., "Enchancement by N–hydroxsulfosuccinimide of water–soluble carbodiimide–mediated coupling reactions" (1986) *Anal. Biochem.* 156:220–222.

Stirchak et al., "Uncharged stereoregular nucleic acid analogs: 2. Morpholino nucleoside oligomers with carbamate internucleoside linkages" (1989) *Nucleic Acids Res.* 17:6129–6141.

Szoka, Francis, Jr., "Comparative properties and methods of preparation of lipid vesicles (liposomes)" (1980) *Ann. Rev. Biophys. Bioeng.* 9:467–508.

Takahashi et al., "Induction of CD8$^+$ cytotoxic T cells by immunization with purified HIV–1 envelope protein in ISCOMs" (1990) *Nature* 344:873–875.

*The Encyclopedia of Molecular Biology,* Sir John Kendrew, ed., Blackwell Science, (Table of Contents).

*The Polymerase Chain Reaction,* (1994) Kary B. Mullis et al., eds., Birkhäuser, (Table of Contents).

Tokunaga et al., "Synthetic oligonucleotides with particular base sequences from the cDNA encoding proteins of *Mycobacterium bovis* BCG induce interferons and activate natural killer cells" (1992) *Microbiol. Immunol.* 36:55–66.

*Transcription and Translation: A Practical Approach,* (1984) Hames, B.D. et al., ed., IRL Press, (Table of Contents).

Tung et al., "Preparation of oligonucleotide–peptide conjugates" (1991) *Bioconjug. Chem.* 2:464–465.

Ulmer et al., "Heterologous protection against influenza by injection of DNA encoding a viral protein" (1993) *Science* 259:1745–1748.

van Neerven et al., "T Cell epitopes of house dust mite major allergen Der p II" (1993) *J. Immunol.* 151:2326–2335.

Waine et al., Nucleic acids: "Vaccines of the future" (1995) *Parasitology Today* 11:113–116.

Wang et al., "Circular RNA oligonucleotides. Synthesis, nucleic acid binding properties, and a comparison with circular DNAs" (1994) *Nucleic Acids Res.* 22:2326–2333.

Warner et al., "Laboratory methods. Construction and evaluation of an instrument for the automated synthesis of oligodeoxyribonucleotides" (1984) *DNA* 3:401–411.

Watwe et al., "Manufacture of liposomes: A review" (1995) *Curr. Sci.* 68:715–724.

Xiang et al., "Manipulation of the immune response to a plasmid–encoded viral antigen by coinoculation with plasmids expressing cytokines" (1995) *Immunity* 2:129–135.

Yamamoto et al., "DNA from bacteria, but not from vertebrates, induces interferons, activates natural killer cells and inhibits tumor growth" (1992) *Microbiol. Immunol.* 36:983–997.

Yamamoto et al., "Ability of oligonucleotides with certain palindromes to induce interferon production and augment natural killer cell activity is associated with their base length" (1994) *Antisense Res. & Develop.* 4:119–122.

Yanagawa et al., "Analysis of superhelical structures of nucleic acid–lipid conjugates by image processing" (1988) *Nucleic Acids Symp. Series* 19:189–192.

Zuckermann et al., "Efficient methods for attachment of thiol specific probes to the 3'–ends of synthetic oligodeoxyribonucleotides" (1987) *Nucleic Acids Res.* 15:5305–5321.

* cited by examiner

SEQUENCE LISTING

<160> NUMBER OF SEQ ID NOS: 11

<210> SEQ ID NO 1
<211> LENGTH: 22
<212> TYPE: DNA
<213> ORGANISM: Artificial sequence
<220> FEATURE:
<223> OTHER INFORMATION: Description of artificial sequence:
      /note=synthetic construct

<400> SEQUENCE: 1
tgactgtgaa cgttcgagat ga                                              22

<210> SEQ ID NO 2
<211> LENGTH: 22
<212> TYPE: DNA
<213> ORGANISM: Artificial sequence
<220> FEATURE:
<223> OTHER INFORMATION: Description of artificial sequence:
      /note=synthetic construct
<221> NAME/KEY: modified_base
<222> LOCATION: (11)...(11)
<223> OTHER INFORMATION: 5-bromocytosine

<400> SEQUENCE: 2
tgactgtgaa ngttccagat ga                                              22

<210> SEQ ID NO 3
<211> LENGTH: 22
<212> TYPE: DNA
<213> ORGANISM: Artificial sequence
<220> FEATURE:
<223> OTHER INFORMATION: Description of artificial sequence:
      /note=synthetic construct

<400> SEQUENCE: 3
tgactgtgaa gcttagagat ga                                              22

<210> SEQ ID NO 4
<211> LENGTH: 22
<212> TYPE: DNA
<213> ORGANISM: Artificial sequence
<220> FEATURE:
<223> OTHER INFORMATION: Description of artificial sequence:
      /note=synthetic construct

<400> SEQUENCE: 4
tcactctctt ccttactctt ct                                              22

<210> SEQ ID NO 5
<211> LENGTH: 22
<212> TYPE: DNA
<213> ORGANISM: Artificial sequence
<220> FEATURE:
<223> OTHER INFORMATION: Description of artificial sequence:
      /note=synthetic construct
<221> NAME/KEY: modified_base
<222> LOCATION: (11)...(11)
<223> OTHER INFORMATION: 5-bromocytosine

<400> SEQUENCE: 5
tgactgtgaa ngttcgagat ga                                              22

<210> SEQ ID NO 6
<211> LENGTH: 22
<212> TYPE: DNA

```
<213> ORGANISM: Artificial sequence
<220> FEATURE:
<223> OTHER INFORMATION: Description of artificial sequence:
      /note=synthetic construct
<221> NAME/KEY: modified_base
<222> LOCATION: (11)...(11)
<223> OTHER INFORMATION: 5-bromocytosine
<221> NAME/KEY: modified_base
<222> LOCATION: (15)...(15)
<223> OTHER INFORMATION: 5-bromocytosine

<400> SEQUENCE: 6
tgactgtgaa ngttngagat ga                                    22

<210> SEQ ID NO 7
<211> LENGTH: 20
<212> TYPE: DNA
<213> ORGANISM: Artificial sequence
<220> FEATURE:
<223> OTHER INFORMATION: Description of artificial sequence:
      /note=synthetic construct
<221> NAME/KEY: modified_base
<222> LOCATION: (8)...(8)
<223> OTHER INFORMATION: 5-bromocytosine

<400> SEQUENCE: 7
tccatgangt tcgtgatcgt                                       20

<210> SEQ ID NO 8
<211> LENGTH: 20
<212> TYPE: DNA
<213> ORGANISM: Artificial sequence
<220> FEATURE:
<223> OTHER INFORMATION: Description of artificial sequence:
      /note=synthetic construct
<221> NAME/KEY: modified_base
<222> LOCATION: (8)...(8)
<223> OTHER INFORMATION: 5-bromocytosine

<400> SEQUENCE: 8
tccataangt tcctgatgct                                       20

<210> SEQ ID NO 9
<211> LENGTH: 20
<212> TYPE: DNA
<213> ORGANISM: Artificial sequence
<220> FEATURE:
<223> OTHER INFORMATION: Description of artificial sequence:
      /note=synthetic construct
<221> NAME/KEY: modified_base
<222> LOCATION: (8)...(8)
<223> OTHER INFORMATION: 5-bromocytosine

<400> SEQUENCE: 9
tccataangt tcgtgatgct                                       20

<210> SEQ ID NO 10
<211> LENGTH: 24
<212> TYPE: DNA
<213> ORGANISM: Artificial sequence
<220> FEATURE:
<223> OTHER INFORMATION: Description of artificial sequence:
      /note=synthetic construct
<221> NAME/KEY: modified_base
<222> LOCATION: (8)...(8)
<223> OTHER INFORMATION: 5-bromocytosine

<400> SEQUENCE: 10
tccataangt tcgcctaacg ttcg                                  24
```

-continued

```
<210> SEQ ID NO 11
<211> LENGTH: 24
<212> TYPE: DNA
<213> ORGANISM: Artificial sequence
<220> FEATURE:
<223> OTHER INFORMATION: Description of artificial sequence:
      /note=synthetic construct
<221> NAME/KEY: modified_base
<222> LOCATION: (8)...(8)
<223> OTHER INFORMATION: 5-bromocytosine
<221> NAME/KEY: modified_base
<222> LOCATION: (19)...(19)
<223> OTHER INFORMATION: 5-bromocytosine

<400> SEQUENCE: 11
tccataangt tcgcctaang ttcg                                        24
```

IMMUNOSTIMULATORY OLIGONUCLEOTIDES WITH MODIFIED BASES AND METHODS OF USE THEREOF

CROSS-REFERENCE TO RELATED APPLICATIONS

The present application claims the priority benefit of U.S. provisional patent application No. 60/088,310 filed Jun. 5, 1998, pending. The aforementioned provisional application is hereby incorporated herein by reference in its entirety.

STATEMENT OF RIGHTS TO INVENTIONS MADE UNDER FEDERALLY SPONSORED RESEARCH

Not Applicable

TECHNICAL FIELD

The present invention relates to immunomodulatory compositions comprising an immunostimulatory oligonucleotide sequence (ISS) in which at least one base has been substituted with a base modified by the addition to C-5 and/or C-6 on cytosine with an electron-withdrawing moiety. It also relates to the administration of said ISS to modulate an immune response.

BACKGROUND ART

The type of immune response generated to infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally determined by the cytokines produced by the cells responding to the antigen. Differences in the cytokines secreted by Th1 and Th2 cells are believed to reflect different biological functions of these two subsets.

The Th1 subset may be particularly suited to respond to viral infections and intracellular pathogens because it secretes IL-2 and IFN-γ, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct patterns of cytokines and so one type of response can moderate the activity of the other type of response. A shift in the Th1/Th2 balance can result in an allergic response, for example, or, alternatively, in an increased CTL response.

Immunization of a host animal against a particular antigen has been accomplished traditionally by repeatedly vaccinating the host with an immunogenic form of the antigen. While most current vaccines elicit effective humoral (antibody, or "Th2-type") responses, they fail to elicit cellular responses (in particular, major histocompatibility complex (MHC) class I-restricted CTL, or "Th1 -type" responses) which are generally absent or weak. For many infectious diseases, such as tuberculosis and malaria, Th2-type responses are of little protective value against infection. Moreover, antibody responses are inappropriate in certain indications, most notably in allergy where an antibody response can result in anaphylactic shock. Proposed vaccines using small peptides derived from the target antigen and other currently used antigenic agents that avoid use of potentially infective intact viral particles, do not always elicit the immune response necessary to achieve a therapeutic effect. The lack of a therapeutically effective human immunodeficiency virus (HIV) vaccine is an unfortunate example of this failure.

Protein-based vaccines typically induce Th2-type immune responses, characterized by high titers of neutralizing antibodies but without significant cell-mediated immunity. In contrast, intradermal delivery of "naked", or uncomplexed, DNA encoding an antigen stimulates immune responses to the antigen with a Th1-type bias, characterized by the expansion of $CD4^+$ T cells producing IFN-γ and cytotoxic $CD8^+$ T cells. Manickan et al. (1995) *J. Immunol.* 155:250–265; Xiang et al. (1995) *Immunity* 2:129–135; Raz et al. (1995) *Proc. Natl. Acad. Sci. USA* 93:5141–5145; and Briode et al. (1997) *J. Allergy Clin. Immunol.* 99:s129. Injection of antigen-encoding naked DNA reproducibly induces both humoral and cellular immune responses against the encoded antigens. Pardoll and Beckerleg (1995) *Immunity* 3:165–169. DNA vaccines can provide a new approach to infectious disease prophylaxis. See, for instance, Dixon (1995) *Bio/Technology* 13:420 and references cited therein.

Certain types of DNA, without being translated, have been shown to stimulate immune responses. Bacterial DNA induces anti-DNA antibodies in injected mice, as well as cytokine production by macrophage and natural killer (NK) cells. Pisetsky (1996) *J. Immunol.* 156:421–423; Shimada et al. (1986) *Jpn. J. Cancer Res.* 77:808–816; Yamamoto et al. (1992a) *Microbiol. Immunol.* 36:983–897; and Cowdery et al. (1996) *J. Immunol.* 156:4570–4575.

B cell and NK cell activation properties of bacterial DNA have been associated with short (6 base pair hexamer) sequences that include a central unmethylated CpG dinucleotide. Yamamoto et al. (1992a); and Krieg et al. (1995) *Nature* 374:546–549. Oligonucleotides comprising a CpG sequence flanked by two 5' purines and two 3' pyrimidines have been shown to be most potent in B cell and NK cell stimulation. For example, when a variety of oligonucleotides comprising hexamers were tested for their ability to augment the NK cell activity of mouse spleen cells, the most immunogenic hexamers included AACGTT, AGCGCT, GACGTC. Yamamoto et al. (1992b) *J. Immunol.* 148:4072–4076. In a study in which B cell activation was measured in response to oligonucleotides, the most stimulatory hexamer sequences (e.g., AACGTC, AACGTT, GACGTC, GACGTT) also matched the sequence of 5'-purine, purine, CG, pyrimidine, pyrimidine-3'. Krieg et al. (1995).

Bacterial DNA stimulated macrophages to produce IL-12 and TNF-α. These macrophage-produced cytokines were found to induce the production of IL-12 and IFN-γ from splenocytes. Halpern et al. (1996) *Cell. Immunol.* 167:72–78. In vitro treatment of splenocytes with either bacterial DNA or CpG containing oligonucleotides induced the production of IL-6, IL-12 and IFN-γ. Klinman et al. (1996) *Proc. Natl. Acad. Sci. USA* 93:2879–2883. Production of all of these cytokines is indicative of induction of a Th1-type immune response rather than a Th2-type response.

Todate, no clear consensus has been reached on the sequences both necessary and sufficient of immune stimulation. A recent study which examined induction of NK activity in response to CpG containing-oligonucleotides suggested that the unmethylated CpG motif was necessary but not sufficient for oligonucleotide induction of NK lytic activity. Ballas et al. (1996) *J. Immunol.* 157:1840–1845. Sequences flanking the CpG appeared to influence the immunostimulatory activity of an oligonucleotide. Immunostimulatory activity of immunostimulatory sequences appears to be independent of adenosine-methylation, and whether the nucleotide is single or double-stranded. See, for example, Tokunaga et al. (1989) *Microbiol Immunol.* 33:929; Tokunaga et al. (1992) *Microbiol. Immunol.* 36:55–66; Yamamoto et al. (1992b); Messina et al. (1993) *Cell. Immunol.* 147:148–157; and Sato et al. (1996) *Science* 273:352–354. Oligonucleotide length also does not seem to be a factor, as double-stranded DNA 4 kb long (Sato et al. (1996)) or single-stranded DNA as short as 15 nucleotides in length (Ballas et al. (1996)) illicited immune responses; though if oligonucleotide length was reduced below 8 bases or if the DNA was methylated with CpG methylase, immunostimulatory activity was abolished. Krieg et al. (1995).

Allergic responses, including those of allergic asthma, are characterized by an early phase response, which occurs within seconds to minutes of allergen exposure and is characterized by cellular degranulation, and a late phase response, which occurs 4 to 24 hours later and is characterized by infiltration of eosinophils into the site of allergen exposure. Specifically, during the early phase of the allergic response, activation of Th2-type lymphocytes stimulates the production of antigen-specific IgE antibodies, which in turn triggers the release of histamine and other mediators of inflammation from mast cells and basophils. During the late phase response, IL-4 and IL-5 production by $CD4^+$ Th2 cells is elevated. These cytokines appear to play a significant role in recruiting eosinophils into site of allergen exposure, where tissue damage and dysfunction result.

Antigen immunotherapy for allergic disorders involves the subcutaneous injection of small, but gradually increasing amounts, of antigen. Such immunization treatments present the risk of inducing IgE-mediated anaphylaxis and do not address the cytokine-mediated events of the allergic late phase response.

Vaccination with certain DNA containing immunostimulatory motifs induces an immune response with a Th1-type bias. For example, mice injected intradermally with *Escherichia coli* (*E. coli*) β-galactosidase (β-Gal) in saline or in the adjuvant alum responded by producing specific IgG1 and IgE antibodies, and $CD4^+$ cells that secreted IL-4 and IL-5, but not IFN-γ, demonstrating that the T cells were predominantly of the Th2 subset. However, mice injected intradermally (or with a tyne skin scratch applicator) with plasmid DNA (in saline) encoding β-Gal and containing an ISS responded by producing IgG2a antibodies and $CD4^+$ cells that secreted IFN-γ, but not IL-4 and IL-5, demonstrating that the T cells were predominantly of the Th1 subset. Moreover, specific IgE production by the plasmid DNA-injected mice was reduced 66–75%. Raz et al. (1996) *Proc. Natl. Acad. Sci. USA* 93:5141–5145. In general, the response to naked DNA immunization is characterized by production of IL-2, TNFα and IFN-γ by antigen-stimulated $CD4^+$ T cells, which is indicative of a Th1-type response. This is particularly important in treatment of allergy and asthma as shown by the decreased IgE production.

In another example, the presence of an immunostimulatory sequence, such as the palindromic hexamer AACGTT, in an antigen-encoding plasmid vector injected intradermally prompted the production of large amounts of IFN-α, IFN-β and IL-12. Sato et al. (1996). IFN-α plays a role in the differentiation of naive T cells toward a Th1-type phenotype, antagonizes Th2 cells, inhibits IgE synthesis, promotes IgG2a production and induces a Th1 phenotype of antigen-specific T cell clones. IL-12 promotes IFN-γ production by T cells and favors maturation of Th1 cells.

It would be useful in treatment of a wide variety of indications to be able to specifically enhance the Th1-type response to a particular antigen while down-regulating the Th2-type response to the same antigen. Treatment or palliation of these indications includes, but is not limited to, tumor therapy, treatment of allergic disorders and induction of a vigorous cellular immune response. The present invention provides compositions comprising oligonucleotide sequences that can be employed in these contexts.

All of the cited literature included in the preceding section, as well as the cited literature included in the following disclosure, are hereby incorporated by reference.

DISCLOSURE OF THE INVENTION

In one embodiment, the ISS comprises a hexameric sequence or hexanucleotide comprising a central CG sequence, where the C residue is modified by the addition to C-5 and/or C-6 with an electron-withdrawing moiety. Preferably, the electron-withdrawing group is a halogen or halogen-containing ligand. Suitable halogens include chlorine, bromine and fluorine. Suitable halogen-containing ligands include, but are not limited to, 5-bromocytosine, 5-fluorocytosine, 5-chlorocytosine, and 5-trifluoromethyl cytosine.

In another embodiment, the modified ISS comprises the general sequence 5'-Purine, Purine, Cytosine, Guanine, Pyrimidine, Pyrimidine-3'. More preferably, the modified ISS comprises the general sequences selected from the group consisting of AACGTC, AACGTT, AGCGTC, AGCGCT, AGCGTT, GACGTC, GACGTT, and GGCGTT. The modified ISS can also comprise any other physiologically acceptable modification.

In another embodiment, the modified ISS comprises the general sequence 5'-Purine, Purine, Cytosine, Guanine, Pyrimidine, Pyrimidine, Cytosine, Cytosine-3'. More preferably, the modified ISS comprises a sequence selected form the group consisting of AACGTTCC and GACGTTCC.

In another embodiment, the modified ISS comprises the general sequence 5'-Purine, Purine, Cytosine, Guanine, Pyrimidine, Pyrimidine, Cytosine, Guanine-3'. More preferably, the modified ISS comprises a sequence selected form the group consisting of AACGTTCG and GACGTTCG.

In another embodiment, the modified ISS comprises the sequence of SEQ ID NO:2.

In another embodiment, the modified ISS comprises the sequence of SEQ ID NO:6.

In another embodiment, the modified ISS comprises the sequence of SEQ ID NO:7.

In another embodiment, the invention provides an immunomodulatory composition comprising a modified ISS and further comprising an antigen.

In another embodiment, the invention provides an immunomodulatory composition comprising a modified ISS in conjunction with a member of the group of immunomodulation facilitators consisting of co-stimulatory molecules, cytokines, chemokines, targeting protein ligand, a trans-activating factor, a peptide, or a peptide comprising a modified amino acid.

In another embodiment, the invention provides an immunomodulatory composition comprising a modified ISS, an antigen and an adjuvant.

The present invention also provides for a method of modulating an immune response comprising the administration of an amount of a modified ISS effective to induce an immune response. Preferably, modulation of an immune response comprises induction of a Th1-type immune response.

In another embodiment, the invention provides methods of treating an individual in need of immune modulation comprising administration of a composition comprising a modified ISS.

MODES FOR CARRYING OUT THE INVENTION

Figure 1:
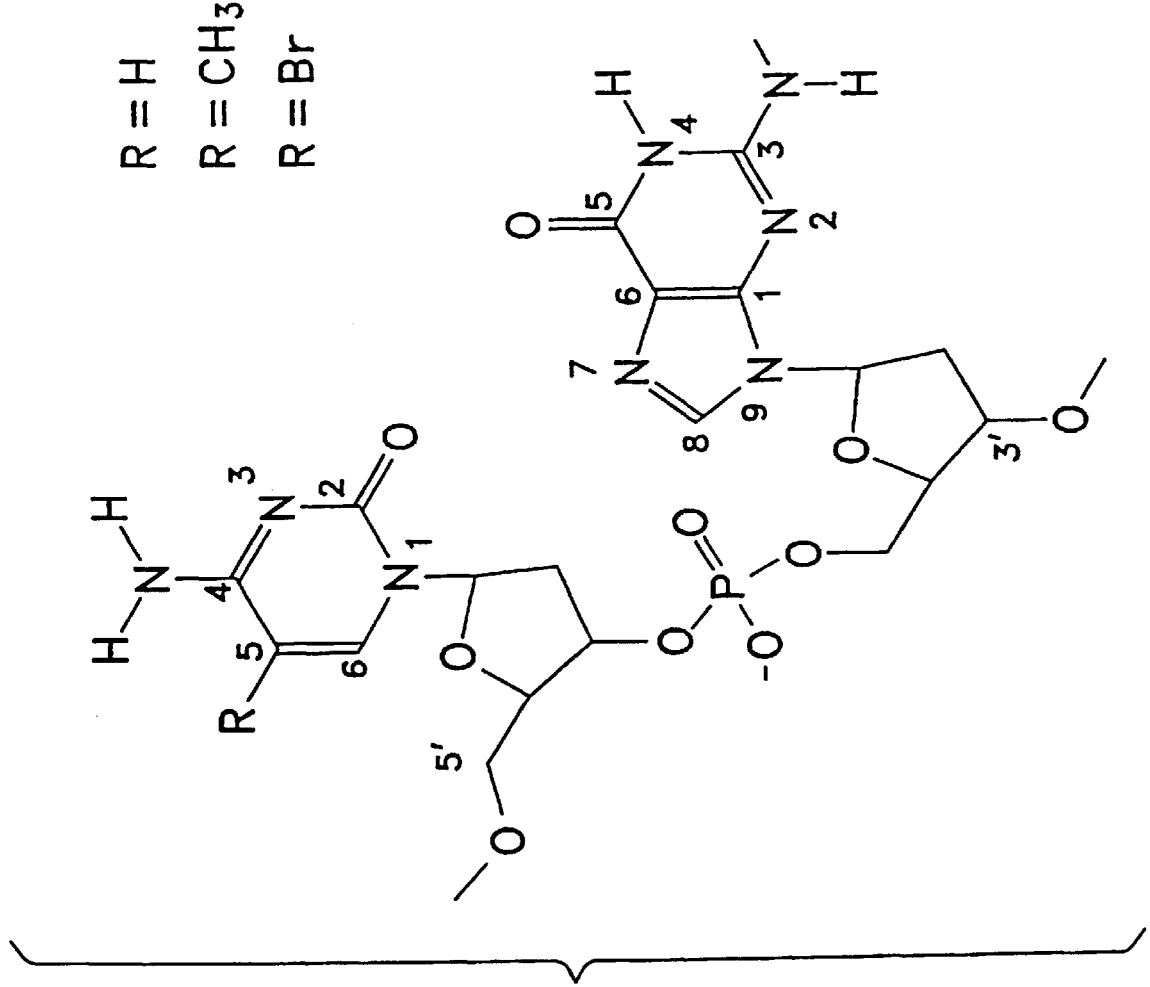
FIG. 1 illustrates the structure of 5-cytosine substituted CpG dinucleotide.

We have discovered modified oligonucleotide sequences capable of modulating an immune response. Such oligonucleotide sequences comprise an immunostimulatory sequence (ISS) comprising a CG dinucleotide in which the C residue is modified by addition to C-5 and/or C-6 of an electron-withdrawing moiety ("modified ISS"). Compositions of the subject invention comprise the modified ISS oligonucleotide alone or in conjunction with an immunomodulatory agent, such as a peptide, an antigen and/or an additional adjuvant. When the same cytosine is methylated, all immunostimulatory activity of the oligonucleotide is lost. Some of the modified ISS have approximately the same, if not greater, immunostimulatory activity relative to the same sequence without a modified base.

Previously described immunostimulatory sequences have comprised a hexamer sequence with a central CpG dinucleotide. The ISS of the present invention comprises any immunostimulatory sequence having the CpG dinucleotide where the C-5 and/or C-6 positions of the C is modified with an electron-withdrawing group. Preferably, the modified ISS contains an hexanucleotide sequence which comprises 5'-purine, purine, cytosine, guanine, pyrimidine, pyrimidine-3'. More preferably, the modified ISS contains an hexanucleotide sequence which comprises 5'-AACGTT-3' or 5'-GACGTT-3'. More preferably, the modified ISS contains an octanucleotide sequence which comprises the previously described hexamer and two additional nucleotides 3' of the hexamer. Preferably, the modified ISS octamer comprises 5'-purine, purine, cytosine, guanine, pyrimidine, pyrimidine, cytosine, guanine-3' or the modified ISS octamer comprises 5'-purine, purine, cytosine, guanine, pyrimidine, pyrimidine, cytosine, cytosine-3'. More preferably, the modified ISS octanucleotide comprises 5'-GACGGTTCG-3' or 5'-GACGTTCC-3'. Still more preferably, the modified ISS octanucleotide comprises 5'-AACGTTCG-3' or 5'-AACGTTCC-3'.

The ISS oligonucleotide of the present invention can comprises any other physiologically acceptable modified nucleotide base. Preferably, in such compositions, the cytosine in the third position from the 5' end can be substituted with a cytosine analog, preferably 5-bromocytidine, fluorinated cytosine, or chlorinated cytosine.

The invention also provides a method and compositions for a general stimulation of an immune response through the adjuvant-like effect of an administered modified ISS.

The present invention also provides methods for the use of a modified ISS in conjunction with an antigen in stimulation of an immune response. Preferably, as used in such methods, the modified ISS provides an adjuvant-like activity in the generation of a Th1-type immune response to the antigen.

Preferably, the immune response stimulated according to the invention is biased toward the Th1-type phenotype and away from the Th2-type phenotype. With reference to the invention, stimulating a Th1-type immune response can be determined in vitro or ex vivo by measuring cytokine production from cells treated with modified ISS as compared to those treated without modified ISS. Methods to determine the cytokine production of cells include those methods described herein and any known in the art. The type of cytokines produced in response to modified ISS treatment indicate a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, and IFN-γ. In contrast, "Th2-type biased cytokines" refers to those associated with a Th2-type immune response, and include, but are not limited to, IL-4, IL-5, IL-10 and IL-13. Cells useful for the determination of ISS activity include cells of the immune system, primary cells isolated from a host and/or cell lines, preferably APCs and lymphocytes, even more preferably macrophages and T cells.

Stimulating a Th1-type immune response can also be measured in a host treated with a modified ISS-antigen composition and can be determined by any method known in the art including, but not limited to: (1) a reduction in levels of IL-4 measured before and after antigen-challenge; or detection of lower (or even absent) levels of IL-4 in a modified ISS-antigen treated host as compared to an antigen-primed, or primed and challenged, control treated without modified ISS; (2) an increase in levels of IL-12, IL-18 and/or IFN (α, β or γ) before and after antigen challenge; or detection of higher levels of IL-12, IL-18 and/or IFN ((α, β or γ) in a modified ISS-antigen treated host as compared to an antigen-primed or, primed and challenged, control treated without modified ISS; (3) IgG2a antibody production in a modified ISS-antigen treated host as compared to a control treated without modified ISS; and/or (4) a reduction in levels of antigen-specific IgE as measured before and after antigen challenge; or detection of lower (or even absent) levels of antigen-specific IgE in a modified ISS-antigen treated host as compared to an antigen-primed, or primed and challenged, control treated without modified ISS. A variety of these determinations can be made by measuring cytokines made by APCs and/or lymphocytes, preferably macrophages and/or T cells, in vitro or ex vivo using methods described herein or any known in the art. Methods to determine antibody production include any known in the art.

The Th1-biased cytokine induction which occurs as a result of modified ISS administration produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

Compositions comprising the Modified ISS

A composition of the subject invention is a modified ISS which is capable of eliciting a desired immune response upon administration. The term "modified ISS" as used herein refers to oligonucleotide sequences that effect a measurable immune response and comprise a CG dinucleotide in which the C residue is modified by addition to C-5 and/or C-6 of an electron-withdrawing moiety. Examples of measurable immune responses include, but are not limited to, antigen-specific antibody production, secretion of cytokines, activation or expansion of lymphocyte populations such as NK cells, CD4$^+$ T lymphocytes, CD8$^+$ T lymphocytes, B lymphocytes, and the like. Preferably, the modified ISS sequences preferentially activate the Th1-type response.

This oligonucleotide can be administered in conjunction with an immunomodulatory molecule, such as an antigen or an immunostimulatory peptide, as described herein. The modified oligonucleotide of the composition contains at least one modified immunostimulatory oligonucleotide sequence ("modified ISS").

The modified ISS preferably comprises a CpG containing sequence, as illustrated in FIG. 1. More preferably, the modified ISS comprises an oligomer of the hexanucleotide sequence 5'-Purine, Purine, CG, Pyrimidine, Pyrimidine-3'. More preferably the modified ISS comprises a hexanucleotide sequence selected from the group consisting of AACGTT and GACGTT. More preferable still, the modified ISS comprises an oligomer of the octanucleotide sequence 5'-Purine, Purine, CG, Pyrimidine, Pyrimidine, Cytosine, Cytosine-3' or the octanucleotide sequence 5'-Purine, Purine, CG, Pyrimidine, Pyrimidine, Cytosine, Guanine-3'. Even more preferably, the modified ISS comprises an octanucleotide selected from the group consisting of AACGTTCC, AACGTTCG, GACGTTCC and GACGTTCG.

Where the oligonucleotide comprises an RNA sequence, the modified ISS preferably comprises a single-stranded or double-stranded sequence selected from the group consisting of AACGUU, GACGUU, AACGUUCC, AACGUUCG, GACGUUCC, and GACGUUCG.

In accordance with the present invention, the oligonucleotide contains at least one modified ISS, and can contain multiple modified ISSs. The modified ISSs can be adjacent within the oligonucleotide, or they can be separated by additional nucleotide bases within the oligonucleotide.

As used interchangeably herein, the terms "oligonucleotide" and "polynucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments.

The ISS can be of any length greater than 6 bases or base pairs, preferably greater than 15 bases or basepairs, more preferably greater than 20 bases or base pairs in length.

In general, dsRNA exerts an immunostimulatory effect and is encompassed by the invention. Further modifications of modified ISS include, but are not limited to, modifications of the 3'OH or 5'OH group, modifications of the nucleotide base, modifications of the sugar component, and modifications of the phosphate group. Various such modifications are described below.

Modified Bases and Base Analogs

Oligonucleotides are polymers of nucleosides joined, generally, through phosphoester linkages. A nucleoside consists of a purine (adenine or guanine or derivative thereof) or pyrimidine (thymine, cytosine or uracil, or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

Multiple bases, sugars, or phosphates in any combination can be substituted in the modified ISS.

The oligonucleotide of the invention can comprise ribonucleotides (containing ribose as the only or principal sugar component), deoxyribonucleotides (containing deoxyribose as the principal sugar component), or, in accordance with the state of the art, modified sugars or sugar analogs can be incorporated in the modified ISS. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the modified ISS, the sugar moiety is preferably the furanoside of ribose, deoxyribose, arabinose or 2'-0-methylribose, and the sugar can be attached to the respective heterocyclic bases either in α or β anomeric configuration. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example.

The phosphorous derivative (or modified phosphate group) which can be attached to the sugar or sugar analog moiety in the oligonucleotides of the present invention can be a monophosphate, diphosphate, triphosphate, alkylphosphate, alkanephosphate, phosphorothioate, phosphorodithioate or the like. A phosphorothiate linkage can be used in place of a phosphodiester linkage. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841–1848; Chaturvedi et al. (1996) *Nucleic Acids Res.*

24:2318–2323; and Schultz et al. (1996) *Nucleic Acids Res.* 24:2966–2973. Preferably, oligonucleotides of the present invention comprise phosphorothioate linkages. Oligonucleotides with phosphorothioate backbones can be more immunogenic than those with phosphodiester backbones and appear to be more resistant to degradation after injection into the host. Braun et al. (1988) *J. Immunol.* 141:2084–2089; and Latimer et al. (1995) *Mol. Immunol.* 32:1057–1064.

The heterocyclic bases, or nucleic acid bases, which are incorporated in the modified ISS can be the naturally-occurring principal purine and pyrimidine bases, (namely uracil or thymine, cytosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the modified ISS can include one or several heterocyclic bases other than the principal five base components of naturally-occurring nucleic acids. Preferably, however, the heterocyclic base in the modified ISS includes, but is not limited to, uracil-5-yl, cytosin-5-yl, adenin-7-yl, adenin-8-yl, guanin-7-yl, guanin-8-yl, 4-aminopyrrolo [2.3-d] pyrimidin-5-yl, 2-amino-4-oxopyrolo [2,3-d] pyrimidin-5-yl, 2-amino-4-oxopyrrolo [2.3-d] pyrimidin-3-yl groups, where the purines are attached to the sugar moiety of the modified ISS via the 9-position, the pyrimidines via the 1-position, the pyrrolopyrimidines via the 7-position and the pyrazolopyrimidines via the 1-position.

A cytosine in the modified ISS can be substituted with a modified cytosine including, but not limited to, azacytosine, 5-bromocytosine, bromouracil, 5-chlorocytosine, chlorinated cytosine, cyclocytosine, cytosine arabinoside, fluorinated cytosine, fluoropyrimidine, fluorouracil, 5,6-dihydrocytosine, halogenated cytosine, halogenated pyrimidine analogue, hydroxyurea, iodouracil, 5-nitrocytosine, 5-trifluoromethyl-cytosine, 5,6-dihydrocytosine, uracil, and any other pyrimidine analog or modified pyrimidine. The present invention also includes dihydrocytosine analogs as potential potent activators of an immune response.

Methods of Modulating Immune Responses with Modified ISS

In one embodiment, the invention provides compositions comprising modified ISS as the only immunologically active substance. Upon administration, such modified ISS induces a stimulation of the immune system.

In other embodiments, modified ISS can be administered in conjunction with one or more members of the group of immunomodulatory molecules comprising antigens (including, but not limited to, proteins, glycoproteins, polysaccharides, and lipids), and/or immunomodulatory facilitators such as co-stimulatory molecules (including, but not limited to, cytokines, chemokines, targeting protein ligand, trans-activating factors, peptides, and peptides comprising a modified amino acid) and adjuvants (including, but not limited to, alum, lipid emulsions, and polylactide/polyglycolide microparticles). The term "immunomodulatory" as used herein includes immunostimulatory as well as immunosuppressive effects. Immunostimulatory effects include, but are not limited to, those that directly or indirectly enhance cellular or humoral immune responses. Examples of immunostimulatory effects include, but are not limited to, increased antigen-specific antibody production; activation or proliferation of a lymphocyte population such as NK cells, $CD4^+$ T lymphocytes, $CD8^+$ T lymphocytes, macrophages and the like; increased synthesis of immunostimulatory cytokines including, but not limited to, IL-1, IL-2, IL-4, IL-5, IL-6, IL-12, IFN-$\gamma$, TNF-$\alpha$ and the like. Immunosuppressive effects include those that directly or indirectly decrease cellular or humoral immune responses. Examples of immunosuppressive effects include, but are not limited to, a reduction in antigen-specific antibody production such as reduced IgE production; activation of lymphocyte or other cell populations that have immunosuppressive activities such as those that result in immune tolerance; and increased synthesis of cytokines that have suppressive effects toward certain cellular functions. One example of this is IFN-$\gamma$, which appears to block IL-4 induced class switch to IgE and IgG1, thereby reducing the levels of these antibody subclasses.

The modified ISS and the antigen and/or immunomodulatory facilitator can be administered together in the form of a conjugate or co-administered in an admixture sufficiently close in time so as to modulate an immune response. Preferably, the modified ISS and immunomodulatory molecule are administered simultaneously. The term "co-administration" as used herein refers to the administration of at least two different substances sufficiently close in time to modulate an immune response. Preferably, co-administration refers to simultaneous administration of at least two different substances.

As used herein, the term "conjugate" refers to a complex in which a modified ISS and an immunomodulatory molecule are linked. Such conjugate linkages include covalent and/or non-covalent linkages.

As used herein, the term "antigen" means a substance that is recognized and bound specifically by an antibody or by a T cell antigen receptor. Antigens can include peptides, proteins, glycoproteins, polysaccharides, gangliosides and lipids; portions thereof and combinations thereof. The antigens can be those found in nature or can be synthetic. Haptens are included within the scope of "antigen." A hapten is a low molecular weight compound that is not immunogenic by itself but is rendered immunogenic when conjugated with an immunogenic molecule containing antigenic determinants.

As used herein, the term "adjuvant" refers to a substance which, when added to an immunogenic agent, nonspecifically enhances or potentiates an immune response to the agent in the recipient host upon exposure to the mixture.

In another embodiment, the invention provides compositions comprising modified ISS and an antigen. Antigens suitable for administration with modified ISS include any molecule capable of eliciting a B cell or T cell antigen-specific response. Preferably, antigens elicit an antibody response specific for the antigen. A wide variety of molecules are antigens. These include, but are not limited to, sugars, lipids and polypeptides, as well as macromolecules such as complex carbohydrates, and phospholipids. Small molecules may need to be haptenized in order to be rendered antigenic. Preferably, antigens of the present invention include peptides, lipids (e.g. sterols, fatty acids, and phospholipids), polysaccharides such as those used in *Hemophilus influenza* vaccines, gangliosides and glycoproteins.

As used herein, the term "peptide" includes peptides and proteins that are of sufficient length and composition to effect a biological response, e.g. antibody production or cytokine activity whether or not the peptide is a hapten. Typically, the peptides are of at least six amino acid residues in length. The term "peptide" further includes modified amino acids, such modifications including, but not limited to, phosphorylation, glycosylation, pegylation, lipidization and methylation.

In one embodiment, the invention provides compositions comprising modified ISS and antigenic peptides. Antigenic peptides can include purified native peptides, synthetic peptides, recombinant proteins, crude protein extracts, attenuated or inactivated viruses, cells, micro-organisms, or fragments of such peptides.

Many antigenic peptides and proteins are known, and available in the art; others can be identified using conventional techniques. Protein antigens that can serve as immunomodulatory facilitators include, but are not limited to, the following examples. Isolated native or recombinant antigens can be derived from plant pollens (see, for example, Rafnar et al. (1991) *J. Biol. Chem.* 266:1229–1236; Breiteneder et al. (1989) *EMBO J.* 8:1935–1938; Elsayed et al. (1991) *Scand. J. Clin. Lab. Invest. Suppl.* 204:17–31; and Malley (1989) *J. Reprod. Immunol.* 16:173–186), dust mite proteins (see, for example, Chua et al. (1988) *J. Exp. Med.* 167:175–182; Chua et al. (1990) *Int. Arch. Allergy Appl. Immunol.* 91:124–129; and Joost van Neerven et al. (1993) *J. Immunol.* 151:2326–2335), animal dander (see, for example, Rogers et al. (1993) *Mol. Immunol.* 30:559–568), animal saliva, bee venom, and fungal spores. Live, attenuated and inactivated microorganisms such as HIV-1, HIV-2, herpes simplex virus, hepatitis A virus (Bradley et al. (1984) *J. Med. Virol.* 14:373–386), rotavirus, polio virus (Jiang et al. (1986) *J. Biol. Stand.* 14:103–109), hepatitis B virus, measles virus (James et al. (1995) *N. Engl. J. Med.* 332:1262–1266), human and bovine papilloma virus, and slow brain viruses can provide peptide antigens. For immunization against tumor formation, immunomodulatory peptides can include tumor cells (live or irradiated), tumor cell extracts, or protein subunits of tumor antigens. Vaccines for immuno-based contraception can be formed by including sperm proteins administered with modified ISS. Lea et al. (1996) *Biochim. Biophys. Acta* 1307:263.

The modified ISS and antigen can be administered as a modified ISS-antigen conjugate and/or they can be co-administered as a complex in the form of an admixture, such as in an emulsion. The association of the modified ISS and the antigen molecules in a modified ISS-antigen conjugate can be through covalent interactions and/or through non-covalent interactions, including high affinity and/or low affinity interactions. Examples of non-covalent interactions that can couple a modified ISS and an antigen in a modified ISS-antigen conjugate include, but are not limited to, ionic bonds, hydrophobic interactions, hydrogen bonds and van der Waals attractions.

In another embodiment, modified ISS can be administered in conjunction with one or more immunomodulatory facilitator. Thus, the invention provides compositions comprising modified ISS and an immunomodulatory facilitator. As used herein, the term "immunomodulatory facilitator" refers to molecules which support and/or enhance the immunomodulatory activity of a modified ISS. Examples of immunomodulatory facilitators can include co-stimulatory molecules, such as cytokines, and/or adjuvants. The modified ISS and facilitator can be administered as a modified ISS-facilitator conjugate and/or they can be co-administered as a complex in the form of an admixture, such as in an emulsion. The association of the modified ISS and the facilitator molecules in a modified ISS-facilitator conjugate can be through covalent interactions and/or through non-covalent interactions, including high affinity and/or low affinity interactions. Examples of non-covalent interactions that can couple a modified ISS and a facilitator in a modified ISS-facilitator conjugate include, but are not limited to, ionic bonds, hydrophobic interactions, hydrogen bonds and van der Waals attractions.

Immunomodulatory facilitators include, but are not limited to, co-stimulatory molecules (such as cytokines, chemokines, targeting protein ligand, trans-activating factors, peptides, and peptides comprising a modified amino acid) and adjuvants (such as alum, lipid emulsions, and polylactide/polyglycolide microparticles).

Among suitable immunomodulatory cytokine peptides for administration with modified ISS are the interleukins (e.g., IL-1, IL-2, IL-3, etc.), interferons (e.g., IFN-$\alpha$, IFN-$\beta$, IFN-$\gamma$), erythropoietin, colony stimulating factors (e.g., G-CSF, M-CSF, GM-CSF) and TNF-$\alpha$. Preferably, immunostimulatory peptides for use in conjunction with modified ISS oligonucleotides are those that stimulate Th1-type immune responses, such as IL-12 (Bliss et al. (1996) *J. Immunol.* 156:887–894), IL-18, TNF-$\alpha$, $\beta$ and $\gamma$, and/or transforming growth factor (TGF)-$\alpha$.

Peptides administered with modified ISS can also include amino acid sequences that mediate protein binding to a specific receptor or that mediate targeting to a specific cell type or tissue. Examples include, but are not limited to, antibodies or antibody fragments, peptide hormones such as human growth hormone, and enzymes. Immunomodulatory peptides also include peptide hormones, peptide neurotransmitters and peptide growth factors. Co-stimulatory molecules such as B7 (CD80), trans-activating proteins such as transcription factors, chemokines such as macrophage chemotactic protein (MCP) and other chemoattractant or chemotactic peptides are also useful peptides for administration with modified ISS.

The modified ISS can also be conjugated to other antigens such as lipids, polysaccharides, gangliosides and the like, through a linking group such as a peptide.

The invention also provides for the administration of modified ISS in conjunction with an adjuvant. Administration of an antigen with a modified ISS and an adjuvant leads to a potentiation of a immune response to the antigen and thus, can result in an enhanced immune response compared to that which results from a composition comprising the modified ISS and antigen alone. Thus, in another embodiment, the invention provides compositions comprising ISS, an antigen and an adjuvant whereby the modified ISS/antigen/adjuvant are co-administered. Preferably, the immunogenic composition contains an amount of an adjuvant sufficient to potentiate the immune response to the immunogen. Preferably, adjuvants include, but are not limited to, oil-in-water emulsions, water-in oil emulsions, alum (aluminum salts), liposomes and microparticles, including but not limited to, polysytrene, starch, polyphosphazene and polylactide/polyglycosides. More preferably, the modified ISS and antigen are co-administered with alum. More preferably, the modified ISS and antigen are co-administered with liposomes. Still more preferably, the modified ISS and antigen are co-administered with an oil-in-water emulsion.

Suitable adjuvants also include, but are not limited to, squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873–875, as well as, lipid-based adjuvants and others described herein. For veterinary use and for production of antibodies in animals, mitogenic components of Freund's adjuvant (both complete and incomplete) can be used.

As with all immunogenic compositions, the immunologically effective amounts of the components must be determined empirically. Factors to be considered include the antigenicity, whether or not modified ISS and/or antigen will be complexed with or covalently attached to an immunomodulatory facilitator, an adjuvant or carrier protein or other carrier, route of administration and the number of immunizing doses to be administered. Such factors are known in the vaccine art and it is well within the skill of immunologists to make such determinations without undue experimentation.

The invention further provides for compositions in which modified ISS and an immunomodulatory molecule(s) are in proximate association at a distance effective to enhance the immune response generated compared to the administration of the modified ISS and the immunomodulatory molecule as an admixture. Thus, the invention provides compositions and methods of use thereof comprising an encapsulating agent that can maintain the proximate association of the modified ISS and immunomodulatory molecule until the complex is available to the target. Preferably, the composition comprising modified ISS, immunomodulatory molecule and encapsulating agent is in the form of adjuvant oil-in-water emulsions, microparticles and/or liposomes. More preferably, adjuvant oil-in-water emulsions, microparticles and/or liposomes encapsulating a modified ISS-immunomodulatory molecule are in the form of particles from about 0.04 μm to about 100 μm in size, more preferably, from about 0.1 μm to about 20 μm, even more preferably, from about 0.15 μm to about 10 μm.

Colloidal dispersion systems, such as microspheres, beads, macromolecular complexes, nanocapsules and lipid-based system, such as oil-in-water emulsions, micelles, mixed micelles and liposomes can provide effective encapsulation of modified ISS-containing compositions.

The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect a modified ISS-containing composition to preserve the immunomodulatory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of semi-synthetic polymers which are suitable for use in the present invention include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

PEGs constitute a diverse group of molecules. A general formula for PEGs is as follows:

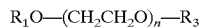

where $R_1$ and $R_3$ are independently H, $H_3C$, OH, or a linear or branched, substituted or unsubstituted alkyl group and n is an integer between 1 and about 1,000. The term "PEG" includes both unsubstituted ($R_1$ and $R_3$=H) as well as substituted PEG. The PEGs for use in encapsulation compositions of the present invention are either purchased from chemical suppliers or synthesized using techniques known to those of skill in the art.

The term "LMS", as used herein, means lamellar lipid particles wherein polar head groups of a polar lipid are arranged to face an aqueous phase of an interface to form membrane structures. Examples of the LMSs include liposomes, micelles, cochleates (i.e., generally cylindrical liposomes), microemulsions, unilamellar vesicles, multilamellar vesicles, and the like.

A preferred colloidal dispersion system of this invention is a liposome. In mice immunized with a liposome-encapsulated antigen, liposomes appeared to enhance a Th1-type immune response to the antigen. Aramaki et al. (1995) *Vaccine* 13:1809–1814. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble chemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). For suitable lipids see e.g., Lasic (1993) "Liposomes: from Physics to Applications" Elsevier, Amsterdam.

Preferably, a liposomal composition is chosen that allows the membrane to be formed with reproducible qualities, such as diameter, and is stable in the presence of elements expected to occur where the liposome is to be used, such as physiological buffers and circulating molecules. Preferably, the liposome is resilient to the effects of manipulation by storage, freezing, and mixing with pharmaceutical excipients.

Lipids suitable for incorporation into lipid membrane structures include, but are not limited to, natural, semi-synthetic or synthetic mono- or di-glycerophospholipids including, but not limited to, phosphatidylcholines (PCs), phosphatidylethanolamines (PEs), phosphatidylglycerols (PGs), phosphatidylinositols (PIs), phosphatidic acids (PAs), phosphatidylserines (PSs), glycero- and cardiolipins. Sphingolipids such as sphingomyelin (SM) and cerebrosides can also be incorporated. While natural phospholipids occur with the phospho moiety at the sn-3 position and hydrophobic chains at the sn-1 and sn-2 positions, synthetic lipids can have alternative stereochemistry with, e.g., the phospho group at the sn-1 or sn-2 positions. Furthermore, the hydrophobic chains can be attached to the glycerol backbone by acyl, ether, alkyl or other linkages. Derivatives of these lipids are also suitable for incorporation into liposomes. Derivatives suitable for use include, but are not limited to, haloalkyl derivatives, including those in which all or some of the hydrogen atoms of the alkyl chains are substituted with, e.g., fluorine. In addition, cholesterol and other amphipathic steroids, bolaamphiphiles (lipids with polar moieties at either end of the molecule which form monolayer membranes) and polyglycerolmonoalkylthers can also be incorporated. Liposomes can be composed of a single lipid or mixtures of two or more different lipids.

In one embodiment, the lipid bilayer of the liposome is formed primarily from phospholipids. Preferably, the phospholipid composition is a complex mixture, comprising a combination of PS and additional lipids such as PC, PA, PE, PG and SM, PI, and/or cardiolipin (diphosphatidylglycerol). If desired, SM can be replaced with a greater proportion of PC, PE, or a combination thereof. PS can be optionally replaced with PG. The composition is chosen so as to confer upon the LMS both stability during storage and administration.

Practitioners of ordinary skill will readily appreciate that each phospholipid in the foregoing list can vary in its structure depending on the fatty acid moieties that are esterified to the glycerol moiety of the phospholipid. Generally, most commercially available forms of a particular phospholipid can be used. However, phospholipids containing particular fatty acid moieties may be preferred for certain applications.

A general process for preparing liposomes containing modified ISS-containing compositions is as follows. An aqueous dispersion of liposomes is prepared from membrane components, such as phospholipids (e.g. PS, PC, PG, SM and PE) and glycolipids according to any known methods. See, e.g., *Ann. Rev. Biophys. Bioeng.* 9:467 (1980). The liposomes can further contain sterols, dialkylphosphates, diacylphosphatidic acids, stearylamine, α-tocopherol, etc., in the liposomal membrane.

To the liposomal dispersion thus prepared is added an aqueous solution of the modified ISS-containing composition and the mixture is allowed to stand for a given period of time, preferably under warming at a temperature above the phase transition temperature of the membrane or above 40° C., followed by cooling to thereby prepare liposomes containing the modified ISS-containing composition in the liposomal membrane.

Alternatively, the desired liposomes can also be prepared by previously mixing the above-described membrane components and modified ISS-containing composition and treating the mixture in accordance with known methods for preparing liposomes.

The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) *Curr. Sci.* 68:715–724. For example, ultrasonication and dialysis methods generally produce small unilamellar vesicles; extrusion and reverse-phase evaporation generally produce larger sized vesicles. Techniques may be combined in order to provide vesicles with the most desirable attributes.

Optionally, the LMS also includes steroids to improve the rigidity of the membrane. Any amount of a steroid can be used. Suitable steroids include, but are not limited to, cholesterol and cholestanol. Other molecules that can be used to increase the rigidity of the membrane include, but are not limited to, cross-linked phospholipids.

Other preferred LMSs for use in vivo are those with an enhanced ability to evade the reticuloendothelial system, which normally phagocytoses and destroys non-native materials, thereby giving the liposomes a longer period in which to reach the target cell. Effective lipid compositions in this regard are those with a large proportion of SM and cholesterol, or SM and PI. LMSs with prolonged circulation time also include those that comprise the monosialoganglioside GM1, glucuronide, or PEG.

The invention encompasses LMSs containing tissue or cellular targeting components. Such targeting components are components of a LMS that enhance its accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The LMSs can be targeted to any cell type toward which a therapeutic treatment is to be directed, e.g., a cell type which can modulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The LMS compositions of the present invention can additionally comprise surfactants. Surfactants can be cationic, anionic, amphiphilic, or nonionic. A preferred class of surfactants are nonionic surfactants; particularly preferred are those that are water soluble. Nonionic, water soluble surfactants include polyoxyethylene derivatives of fatty alcohols, fatty acid ester of fatty alcohols and glyceryl esters, wherein the polyoxyethylene group is coupled via an ether linkage to an alcohol group. Examples include, but are not limited to, polyoxyethylene sorbitan fatty acid esters, polyoxyethylene castor oil derivatives, polyoxyethylene hardened castor oil derivatives, fatty acid sodium salts, sodium cholates, polyexyethylene fatty acid ester and polyoxyethylene alkyl ethers.

The LMS compositions encompassed herein include micelles. The term "micelles" as used herein means aggregates which form from tenside molecules in aqueous solutions above a specific temperature (Krafft point) or a characteristic concentration, the critical micellization concentration (cmc). When the cmc is exceeded, the monomer concentration remains practically constant and the excess tenside molecules form micelles. Micelles are thermodynamically stable association colloids of surfactant substances in which the hydrophobic radicals of the monomers lie in the interior of the aggregates and are held together by hydrophobic interaction; the hydrophilic groups face the water and by solvation provide the solubility of the colloid. Micelles occur in various shapes (spheres, rods, discs) depending on the chemical constitution of the tenside and on the temperature, concentration or ionic strength of the solution. Reaching the cmc is manifest by abrupt changes in surface tension, osmotic pressure, electrical conductivity and viscosity.

A process for preparing micelles containing modified ISS-containing compositions is as follows. A micelle-forming surfactant, such as polyoxyethylene sorbitan fatty acid esters, polyoxyethylene castor oil derivatives, polyoxyethylene hardened castor oil derivatives, fatty acid sodium salts, sodium cholates, polyoxyethylene fatty acid ester, and polyoxyethylene alkyl ethers, alkyl glycosides, is added to water at a concentration above the cmc to prepare a micellar dispersion. To the micellar dispersion is added an aqueous solution of a modified ISS-containing composition and the mixture is allowed to stand for a given period of time, preferably under warming at 40° C. or higher, followed by cooling, to thereby prepare micelles containing modified ISS-containing compositions in the micellar membrane. Alternatively, the desired micelles can also be prepared by previously mixing the above-described micelle-forming substances and modified ISS-containing compositions and treating the mixture according to known methods for micelle formation.

Synthesis of the Modified ISS
a) Modified ISS

The modified ISS can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Chemical synthesis of oligonucleotides can involve conventional automated methods, such as the phosphoramidite method disclosed by Warner et al. (1984) *DNA* 3:401. See also U.S. Pat. No. 4,458,066. Oligonucleotide degradation can be accomplished through the exposure of an oligonucleotide to a nuclease, as exemplified in U.S. Pat. No. 4,650,675.

The modified ISS can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular modified ISS can be isolated, synthesized through recombinant methods, or chemically synthesized. Where the circular modified ISS is obtained through isolation or through recombinant methods, the modified ISS will preferably be a plasmid. The chemical synthesis of smaller circular oligonucleotides can be performed using any method described in the literature. See, for instance, Gao et al. (1995) *Nucleic Acids Res.* 23:2025–2029; and Wang et al. (1994) *Nucleic Acids Res.* 22:2326–2333.

The modified ISS can also contain phosphorous based modified oligonucleotides. These can be synthesized using standard chemical transformations. The efficient solid-support based construction of methylphosphonates has also been described. The synthesis of other phosphorous based modified oligonucleotides, such as phosphotriesters (Miller et al. (1971) *JACS* 93:6657–6665), phosphoramidates (Jager et al. (1988) *Biochem.* 27:7247–7246), and phosphorodithioates (U.S. Pat. No. 5,453,496) has also been described. Other non-phosphorous based modified oligonucleotides can also be used. Stirchak et al. (1989) *Nucleic Acids Res.* 17:6129–6141.

The techniques for making phosphate group modifications to oligonucleotides are known in the art. For review of one such useful technique, an intermediate phosphate triester for the target oligonucleotide product is prepared and oxidized to the naturally occurring phosphate triester with aqueous iodine or with other agents, such as anhydrous amines. The resulting oligonucleotide phosphoramidates can be treated with sulfur to yield phosphorothioates. The same general technique (excepting the sulfur treatment step) can be applied to yield methylphosphoamidites from methylphosphonates. See also, U.S. Pat. Nos. 4,425,732; 4,458,066; 5,218,103; and 5,453,496.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

b) Immunomodulatory Molecules

Attenuated and inactivated viruses are suitable for use herein as the antigen. Preparation of these viruses is well-known in the art. Polio virus can be inactivated by chemical agents such as beta-propiolactone. Jiang et al. (1986). The growth of attenuated strains of Hepatitis A virus has been described (Bradley et al. (1984)), as well as the growth of attenuated measles virus (James et al. (1995). Additionally, attenuated and inactivated viruses such as HIV-1, HIV-2, herpes simplex virus, hepatitis B virus, rotavirus, human and non-human papillomavirus and slow brain viruses can provide peptide antigens.

Allergens are suitable for use herein as immunomodulatory molecules. Preparation of many allergens is well-known in the art, including, but not limited to, preparation of ragweed pollen allergen Antigen E (Amb al) (Rafnar et al. 1991), major dust mite allergens Der pI and Der PII (Chua et al. (1988); and Chua et al. (1990)), white birch pollen Betvl (Breitneder et al. 1989), domestic cat allergen Fel dI (Rogers et al. (1993), and protein antigens from tree pollen (Elsayed et al. (1991)). Preparation of protein antigens from grass pollen for in vivo administration has been reported. Malley (1989).

Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362:833–839. Proteolytic enzymes can also be utilized to couple amino acids to produce peptides. Kullmann (1987) *Enzymatic Peptide Synthesis*, CRC Press, Inc. Alternatively, the peptide can be obtained by using the biochemical machinery of a cell, or by isolation from a biological source. Recombinant DNA techniques can be employed for the production of peptides. Hames et al. (1987) *Transcription and Translation: A Practical Approach*, IRL Press. Peptides can also be isolated using standard techniques such as affinity chromatography.

Preferably the antigens are peptides, lipids (e.g. sterols, fatty acids, and phospholipids), polysaccharides such as those used in *H. influenza* vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

c) Modified ISS-Immunomodulatory Molecule Conjugates

The modified ISS portion can be coupled with the immunomodulatory molecule portion of a conjugate in a variety of ways, including covalent and/or non-covalent interactions.

The link between the portions can be made at the 3' or 5' end of the modified ISS, or at a suitably modified base at an internal position in the modified ISS. If the immunomodulatory molecule is a peptide and contains a suitable reactive group (e.g., an N-hydroxysuccinimide ester) it can be reacted directly with the $N^4$ amino group of cytosine residues. Depending on the number and location of cytosine residues in the modified ISS, specific labeling at one or more residues can be achieved.

Alternatively, modified oligonucleosides, such as are known in the art, can be incorporated at either terminus, or at internal positions in the modified ISS. These can contain blocked functional groups which, when deblocked, are reactive with a variety of functional groups which can be present on, or attached to, the immunomodulatory molecule of interest.

Where the immunomodulatory molecule is a peptide, this portion of the conjugate can be attached to the 3'-end of the modified ISS through solid support chemistry. For example, the modified ISS portion can be added to a polypeptide portion that has been pre-synthesized on a support. Haralambidis et al. (1990a) *Nucleic Acids Res.* 18:493–499; and Haralambidis et al. (1990b) *Nucleic Acids Res.* 18:501–505. Alternatively, the modified ISS can be synthesized such that it is connected to a solid support through a cleavable linker extending from the 3'-end. Upon chemical cleavage of the modified ISS from the support, a terminal thiol group is left at the 3'-end of the oligonucleotide (Zuckermann et al. (1987) *Nucleic Acids Res.* 15:5305–5321; and Corey et al. (1987) *Science* 238:1401–1403) or a terminal amine group is left at the 3'-end of the oligonucleotide (Nelson et al. (1989) *Nucleic Acids Res.* 17:1781–1794). Conjugation of the amino-modified modified ISS to amino groups of the peptide can be performed as described in Benoit et al. (1987) *Neuromethods* 6:43–72. Conjugation of the thiol-modified modified ISS to carboxyl groups of the peptide can be performed as described in Sinah et al. (1991) *Oligonucleotide Analogues: A Practical Approach*, IRL Press. Coupling of an oligonucleotide carrying an appended maleimide to the thiol side chain of a cysteine residue of a peptide has also been described. Tung et al. (1991) *Bioconjug. Chem.* 2:464–465.

The peptide portion of the conjugate can be attached to the 5'-end of the modified ISS through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) *Nucleic Acids Res.* 14:6227–6245; Connolly (1985) *Nucleic Acids Res.* 13:4485–4502; Kremsky et al. (1987) *Nucleic Acids Res.* 15:2891–2909; Connolly (1987) *Nucleic Acids Res.* 15:3131–3139; Bischoffet al. (1987) *Anal. Biochem.* 164:336–344; Blanks et al. (1988) *Nucleic Acids Res.* 16:10283–10299; and U.S. Pat. Nos. 4,849,513, 5,015,733, 5,118,800, and 5,118,802. Subsequent to deprotection, the latent amine, thiol, and carboxyl functionalities can be used to covalently attach the oligonucleotide to a peptide. Benoit et al. (1987); and Sinah et al. (1991).

The peptide portion can be attached to a modified cytosine or uracil at any position in the modified ISS. The incorporation of a "linker arm" possessing a latent reactive functionality, such as an amine or carboxyl group, at C-5 of the modified base provides a handle for the peptide linkage. Ruth, *4th Annual Congress for Recombinant DNA Research*, p. 123.

A modified ISS-immunomodulatory molecule conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an ISS. Roget et al. (1989) *Nucleic Acids Res.* 17:7643–7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving a modified ISS and residues within the immunomodulatory molecule, such as charged amino acids, or through the use of a linker portion comprising charged residues that can interact with both the oligonucleotide and the immunomodulatory molecule. For example, non-covalent conjugation can occur between a generally negatively-charged modified ISS and positively-charged amino acid residues of a peptide, e.g., polylysine and polyarginine residues.

Non-covalent conjugation between modified ISS and immunomodulatory molecules can occur through DNA binding motifs of molecules that interact with DNA as their natural ligands. For example, such DNA binding motifs can be found in transcription factors and anti-DNA antibodies.

The linkage of the modified ISS to a lipid can be formed using standard methods. These methods include, but are not limited to, the synthesis of oligonucleotide-phospholipid conjugates (Yanagawa et al. (1988) *Nucleic Acids Symp. Ser.* 19:189–192), oligonucleotide-fatty acid conjugates (Grabarek et al. (1990) *Anal. Biochem.* 185:131–135; and Staros et al. (1986) *Anal. Biochem.* 156:220–222), and oligonucleotide-sterol conjugates. Boujrad et al. (1993) *Proc. Natl. Acad. Sci. USA* 90:5728–5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347–355.

The linkage of a circular modified ISS to a peptide or antigen can be formed in several ways. Where the circular modified ISS is synthesized using recombinant or chemical methods, a modified nucleoside is suitable. Ruth (1991) in *Oligonucleotides and Analogues: A Practical Approach*, IRL Press. Standard linking technology can then be used to connect the circular modified ISS to the antigen or other peptide. Goodchild (1990) *Bioconjug. Chem.* 1:165. Where the circular modified ISS is isolated, or synthesized using recombinant or chemical methods, the linkage can be formed by chemically activating, or photoactivating, a reactive group (e.g. carbene, radical) that has been incorporated into the antigen or other peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) *Nonisotopic DNA Probe Techniques*, Academic Press; and Geoghegan et al. (1992) *Bioconjug Chem.* 3:138–146.

Assessment of Immune Response to Modified ISS

Analysis (both qualitative and quantitative) of the immune response to modified ISS-containing compositions can be by any method known in the art, including, but not limited to, measuring antigen-specific antibody production, activation of specific populations of lymphocytes such as $CD4^+$ T cells or NK cells, and/or production of cytokines such as IFN, IL-2, IL-4, or IL-12. Methods for measuring specific antibody responses include enzyme-linked immunosorbent assay (ELISA) and are well known in the art. Measurement of numbers of specific types of lymphocytes such as $CD4^+$ T cells can be achieved, for example, with fluorescence-activated cell sorting (FACS). Cytotoxicity assays can be performed for instance as described in Raz et al. (1994) *Proc. Natl. Acad. Sci. USA* 91:9519–9523. Serum concentrations of cytokines can be measured, for example, by ELISA. These and other assays to evaluate the immune response to an immunogen are well known in the art. See, for example, *Selected Methods in Cellular Immunology* (1980) Mishell and Shiigi, eds., W. H. Freeman and Co.

Administration of the Modified ISS

The modified ISS can be administered alone or in combination with other pharmaceutical and/or immunogenic and/or immunostimulatory agents and can be combined with a physiologically acceptable carrier thereof. The effective amount and method of administration of the particular modified ISS formulation can vary based on the individual patient and the stage of the disease and other factors evident to one skilled in the art. The route(s) of administration useful in a particular application are apparent to one of skill in the art. Routes of administration include but are not limited to topical, dermal, transdermal, transmucosal, epidermal parenteral, gastrointestinal, and naso-pharyngeal and pulmonary, including transbronchial and transalveolar. A suitable dosage range is one that provides sufficient modified ISS-containing composition to attain a tissue concentration of about 1–10 $\mu$M as measured by blood levels. The absolute amount given to each patient depends on pharmacological properties such as bioavailability, clearance rate and route of administration.

As described herein, APCs and tissues with high concentration of APCs are preferred targets for the modified ISS-containing compositions. Thus, administration of modified ISS to mammalian skin and/or mucosa, where APCs are present in relatively high concentration, is preferred.

The present invention provides modified ISS-containing compositions suitable for topical application including, but not limited to, physiologically acceptable implants, ointments, creams, rinses and gels. Topical administration is, for instance, by a dressing or bandage having dispersed therein a delivery system, or by direct administration of a delivery system into incisions or open wounds. Creams, rinses, gels or ointments having dispersed therein a modified ISS-containing composition are suitable for use as topical ointments or wound filling agents.

Preferred routes of dermal administration are those which are least invasive. Preferred among these means are transdermal transmission, epidermal administration and subcutaneous injection. Of these means, epidermal administration is preferred for the greater concentrations of APCs expected to be in intradermal tissue.

Transdermal administration is accomplished by application of a cream, rinse, gel, etc. capable of allowing the modified ISS-containing composition to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference.

For transdermal transmission, iontophoresis is a suitable method. Iontophoretic transmission can be accomplished using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or periodically. Preparation and use of the patch should be performed according to the manufacturer's printed instructions which accompany the LECTRO PATCH product; those instructions are incorporated herein by this reference.

For transdermal transmission, low-frequency ultrasonic delivery is also a suitable method. Mitragotri et al. (1995) *Science* 269:850–853. Application of low-frequency ultrasonic frequencies (about 1 MHz) allows the general controlled delivery of therapeutic compositions, including those of high molecular weight.

Epidermal administration essentially involves mechanically or chemically irritating the outermost layer of the epidermis sufficiently to provoke an immune response to the irritant. Specifically, the irritation should be sufficient to attract APCs to the site of irritation.

An exemplary mechanical irritant means employs a multiplicity of very narrow diameter, short tines which can be used to irritate the skin and attract APCs to the site of irritation, to take up modified ISS-containing compositions transferred from the end of the tines. For example, the MONO-VACC old tuberculin test manufactured by Pasteur Merieux of Lyon, France contains a device suitable for introduction of modified ISS-containing compositions.

The device (which is distributed in the U.S. by Connaught Laboratories, Inc. of Swiftwater, Pa.) consists of a plastic container having a syringe plunger at one end and a tine disk at the other. The tine disk supports a multiplicity of narrow diameter tines of a length which will just scratch the outermost layer of epidermal cells. Each of the tines in the MONO-VACC kit is coated with old tuberculin; in the present invention, each needle is coated with a pharmaceutical composition of modified ISS-containing composition.

Use of the device is preferably according to the manufacturer's written instructions included with the device product. Similar devices which can also be used in this embodiment are those which are currently used to perform allergy tests.

Another suitable approach to epidermal administration of modified ISS is by use of a chemical which irritates the outermost cells of the epidermis, thus provoking a sufficient immune response to attract APCs to the area. An example is a keratinolytic agent, such as the salicylic acid used in the commercially available topical depilatory creme sold by Noxema Corporation under the trademark NAIR. This approach can also be used to achieve epithelial administration in the mucosa. The chemical irritant can also be applied in conjunction with the mechanical irritant (as, for example, would occur if the MONO-VACC type tine were also coated with the chemical irritant). The modified ISS can be suspended in a carrier which also contains the chemical irritant or coadministered therewith.

Another delivery method for administering modified ISS-containing compositions makes use of non-lipid polymers, such as a synthetic polycationic amino polymer. Leff (1997) *Bioworld* 86:1–2.

Parenteral routes of administration include but are not limited to electrical (iontophoresis) or direct injection such as direct injection into a central venous line, intravenous, intramuscular, intraperitoneal, intradermal, or subcutaneous injection. Compositions suitable for parenteral administration include, but are not limited to, pharmaceutically acceptable sterile isotonic solutions. Such solutions include, but are not limited to, saline and phosphate buffered saline for injection of the modified ISS-containing compositions.

Gastrointestinal routes of administration include, but are not limited to, ingestion and rectal. The invention includes modified ISS-containing compositions suitable for gastrointestinal administration including, but not limited to, pharmaceutically acceptable, powders, pills or liquids for ingestion and suppositories for rectal administration.

Naso-pharyngeal and pulmonary routes of administration include, but are not limited to, by-inhalation, transbronchial and transalveolar routes. The invention includes ISS-containing compositions suitable for by-inhalation administration including, but not limited to, various types of aerosols for inhalation, as well as powder forms for delivery systems. Devices suitable for by-inhalation administration of modified ISS-containing compositions include, but are not limited to, atomizers and vaporizers. Atomizers and vaporizers filled with the powders are among a variety of devices suitable for use in by-inhalation delivery of powders. See, e.g., Lindberg (1993) Summary of Lecture at Management Forum 6–7 December 1993 "Creating the Future for Portable Inhalers."

The methods of producing suitable devices for injection, topical application, atomizers and vaporizers are known in the art and will not be described in detail.

The choice of delivery routes can be used to modulate the immune response elicited. For example, IgG titers and CTL activities were identical when an influenza virus vector was administered via intramuscular or epidermal (gene gun) routes; however, the muscular inoculation yielded primarily IgG2A, while the epidermal route yielded mostly IgG1. Pertmer et al. (1996) *J. Virol.* 70:6119–6125. Thus, one of skill in the art can take advantage of slight differences in immunogenicity elicited by different routes of administering the immunomodulatory oligonucleotides of the present invention.

The above-mentioned compositions and methods of administration are meant to describe but not limit the methods of administering the modified ISS-containing compositions of the invention. The methods of producing the various compositions and devices are within the ability of one skilled in the art and are not described in detail here.

The following examples are provided to illustrate but not limit the invention.

EXAMPLES

Example 1

Stimulation of Cytokine Production by Oligonucleotides Comprising Modified ISS

Several oligonucleotides comprising modified ISS were tested for their immunostimulatory activity on mouse splenocytes and on human peripheral blood mononuclear cells (hPBMCs). Immunostimulation in response to oligonucleotide was assessed by measurement of cytokine secretion into the culture media and by cell proliferation. Cytokine levels in the culture supernatant were determined by enzyme-linked immunosorbent assay (ELISA) tests.

The oligonucleotides were synthesized using standard solid phase oligonucleotide techniques. The solid phase ready analog monomers were purchased from Glen Research, Sterling, Va. and included in the standard manner in a solid phase oligonucleotide synthesizer. The synthesis of the oligonucleotides were performed by TriLink BioTechnologies Inc., San Diego, Calif.

Cells were isolated and prepared using standard techniques. hPBMCs were isolated from heparinized peripheral blood from healthy donors by ficoll Hypaque gradients. Spleens of BALB/c mice were harvested and the splenocytes isolated using standard teasing and treatment with ACK lysing buffer from Bio Whittaker, Inc. Isolated cells were washed in RPMI 1640 media supplemented with 2% heat-inactivated fetal calf serum (FCS), 50 $\mu$M 2-mercaptoethanol, 1% penicillin-streptomycin, and 2 mM L-glutamine and resuspended at approximately $4 \times 10^6$ cells/ml in 10%FCS/RPMI (RPMI 1640 media with 10% heat-inactivated FCS, 50 $\mu$M 2-mercaptoethanol, 1% penicillin-streptomycin, and 2 mM L-glutamine).

Generally, cell cultures were set up in triplicate with approximately $4 \times 10^5$ cells/well in a 96-well, flat microtiter plate in 100 $\mu$l 10%FCS/RPMI with the cells allowed to rest for at lest 1 hour after plating. For oligonucleotide activity assays, oligonucleotides were diluted in 10%FCS/RPMI and 100 $\mu$l of the desired oligonucleotide dilution was added to the appropriate well. In general, final oligonucleotide concentrations included 0.1 $\mu$g/ml, 1.0 $\mu$g/ml, and 10 $\mu$g/ml. Cells were then incubated for 1, 2, or 3 days.

To determine cell proliferation, 100 $\mu$l of supernatant was harvested from each well on appropriate days, pulsed with 1.0 $\mu$M tritiated thymidine and incubated overnight. Standard methods to assess tritiated thymidine incorporation were used to determine cell proliferation. Cytokine production by the cells was determined by ELISAs of culture supernatant using commercially-available antibodies to the cytokines. Examples of results of such experiments are graphically depicted in FIGS. 2–4. The oligonucleotides used included the following:

TABLE 1

| SEQ ID NO: | Oligonucleotide Sequence | |
|---|---|---|
| 1 | tgactgt<u>aacgttcg</u>agatga | ISS (bold, underline) |
| 2 | tgactgt<u>aabgttcc</u>agatga | b = 5-bromo-cytosine |
| 3 | tgactgtgaagcttagagatga | no ISS |
| 4 | tcactctcttccttactcttct | no ISS |
| 5 | tgactgt<u>aabgttcg</u>agatga | b = 5-bromo-cytosine |
| 6 | tgactgt<u>aabgttbg</u>agatga | b = 5-bromo-cytosine |
| 7 | tccat<u>gabgttcg</u>tgatcgt | b = 5-bromo-cytosine |
| 8 | tccat<u>aabgttcc</u>tgatgct | b = 5-bromo-cytosine |
| 9 | tccat<u>aabgttcg</u>tgatgct | b = 5-bromo-cytosine |
| 10 | tccat<u>aabgttcg</u>cct<u>aacgttcg</u> | b = 5-bromo-cytosine |
| 11 | tccat<u>aabgttcg</u>cct<u>aabgttcg</u> | b = 5-bromo-cytosine |

Figure 2:
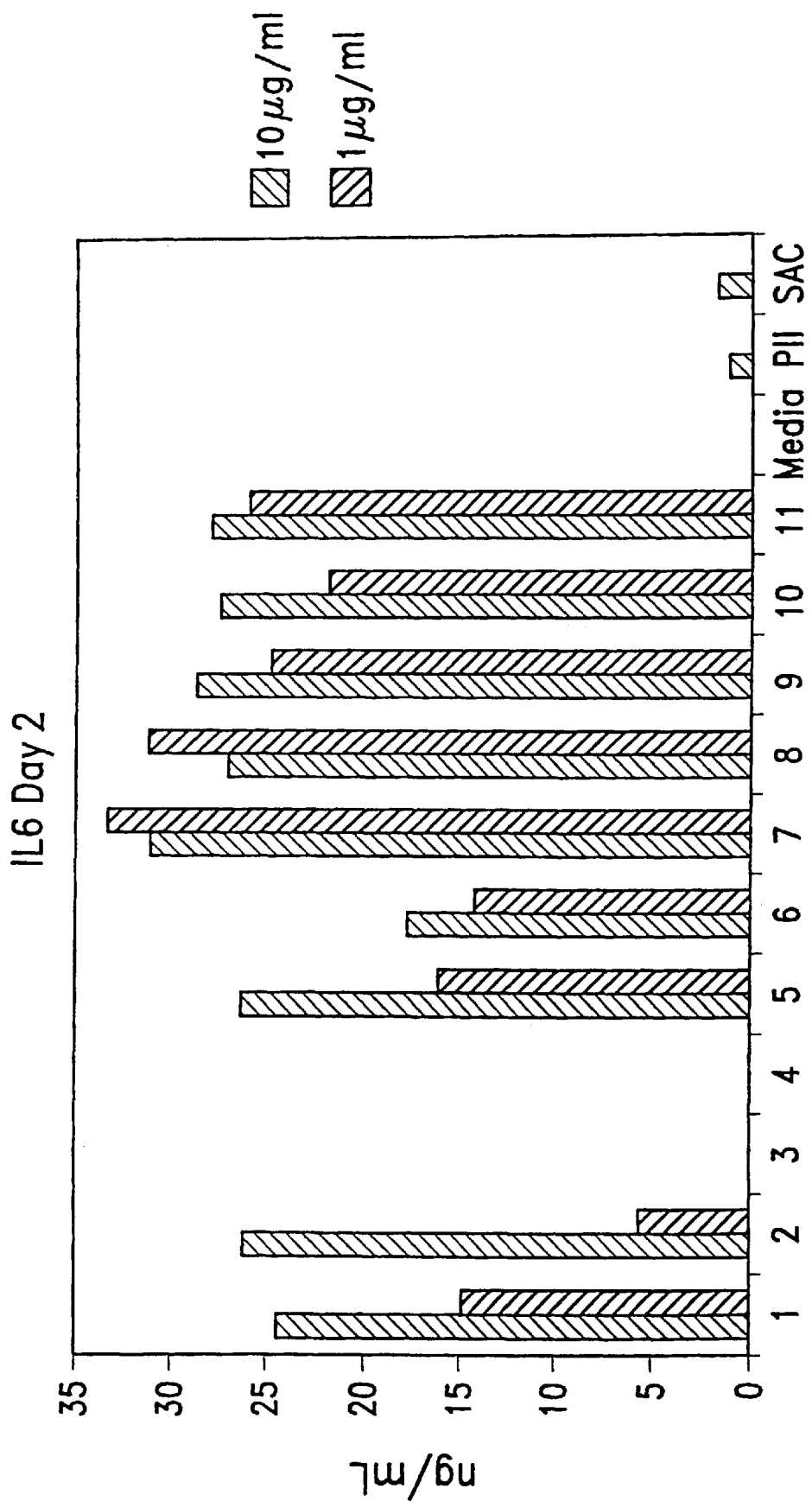
FIG. 2 presents a graph depicting the level of IL-6 found in the culture supernatant of splenocytes after exposure to oligonucleotides for 48 hours. See Table 1 for identification of oligonucleotides SEQ ID NOs: 1–11 indicated at the bottom of the graph.
Figure 3:
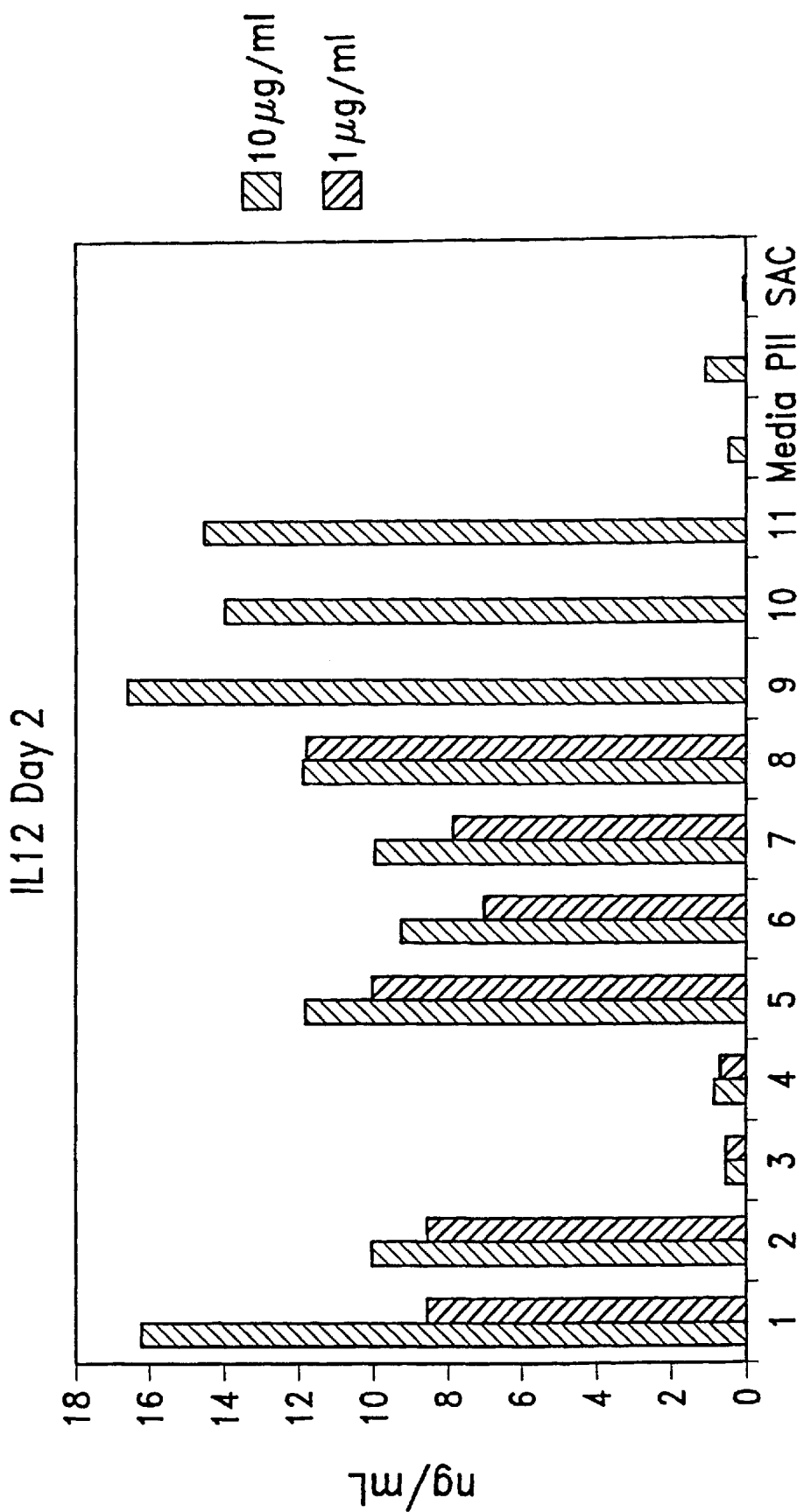
FIG. 3 presents a graph depicting the level of IL-12 found in the culture supernatant of splenocytes after exposure to oligonucleotides for 48 hours. See Table 1 for identification of oligonucleotides SEQ ID NOs: 1–11 indicated at the bottom of the graph.
Figure 4:
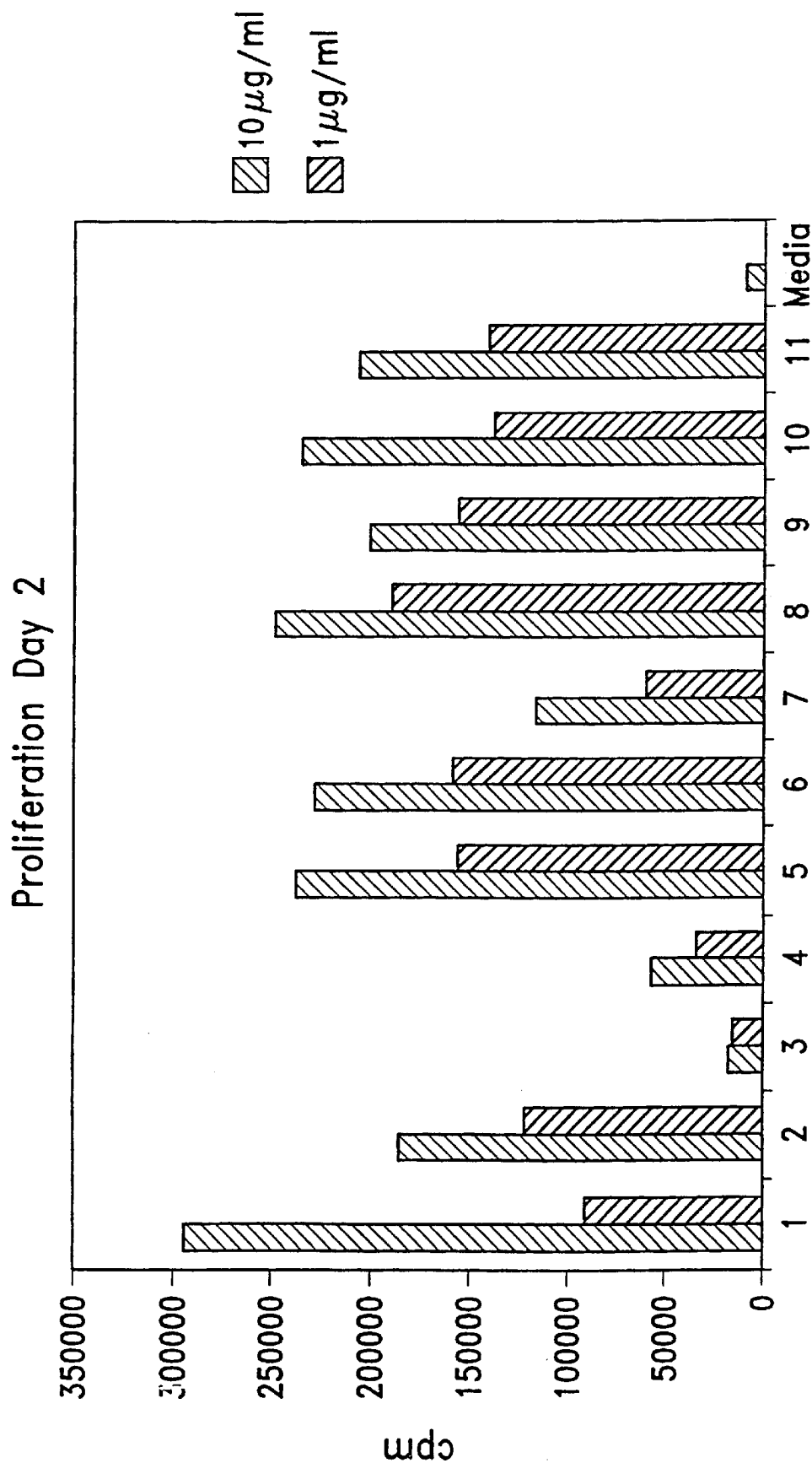
FIG. 4 presents a graph showing the efficacy of various oligonucleotides comprising modified cytosines to stimulate proliferation of splenocytes. Cell proliferation determined after 48 hours in culture. See Table 1 for identification of oligonucleotides SEQ ID NOs: 1–11 indicated at the bottom of the graph.

Results from an experiment in which mouse splenocytes were treated with 10 μg/ml or 1 μg/ml of the oligonucleotides listed in Table 1 are depicted in FIGS. 2–4. Treatment of the cells with oligonucleotides comprising at least one ISS resulted in the production of IL-6 and IL-12 from the cells, as well as a stimulation of cell proliferation. See, for example, FIGS. 2–4, oligonucleotide 1. The oligonucleotides comprising a modified ISS were, in general, as effective as or more effective than the oligonucleotide with an unmodified ISS. See, for example, FIGS. 2–4, oligonucleotides 2, 5–11. Oligonucleotides without an ISS were unable to stimulate IL-6 or IL-12 production or cell proliferation. See, for example, FIGS. 2–4, oligonucleotides 3 and 4. All oligonucleotides used in this experiment contained a phosphorothioate backbone.

Example 2

Potentiation of an Immune Response with Adjuvant Co-administration

The effect of adjuvant co-administration with antigen and modified ISS (mISS) on an immune response to the antigen is examined using the adjuvants alum and MF59. Compositions comprising 1 μg AgE, a major allergic component is short ragweed, is injected intradermally into mice at week 0, 2, and 4. Antigen compositions usable are listed below:

| | |
|---|---|
| AgE | AgE-mISS conjugate |
| AgE + mISS mix (equivalent) | AgE + mISS mix (50 μg mISS) |
| AgE and MF59 | AgE-mISS conjugate and MF59 |
| AgE and alum (25 μg) | AgE-mISS conjugate and alum (25 μg) |
| AgE and alum (800 μg) | |

The amount of anti-AgE antibody in the serum of the mice is determined at day 0 and weeks 2, 4, and 6. Anti-AgE antibody assays (IgE, IgG1, IgG2a) are performed by ELISA tests using the original AgE vaccine as the coated antigen on microtiter plates as described in Raz et al. (1996).

A comparison of anti-AgE antibody production, including anti-AgE antibody subtypes, provides an indication as to the level and type of immune response that results from each administered composition.

Example 3

Selective Induction of a Th1-type Response in a Host after Administration of a Composition Comprising a Modified ISS In mice, IgG2A antibodies are serological markers for a Th1-type immune response, whereas IgG1 antibodies are indicative of a Th2-type immune response. The production of the cytokine IFN-γ is also an indicator of a Th1-type response.

To determine which response, if any, would be produced by mice who received modified ISS compositions according to the invention, groups of BALB/c mice are immunized with 10 μg β-galactosidase (β-Gal) protein. Some mice receive β-Gal alone, some receive a modified ISS-β-Gal conjugate, some receive a modified ISS-β-Gal-adjuvant composition, and some receive a composition of β-Gal with a nonstimulatory oligonucleotide. Naive mice are also included in the experiment.

At two week intervals, any IgG2A and IgG1 to β-Gal present in the serum of each mouse is measured by ELISA on microtiter pates coated with β-Gal. The titers of anti-β-Gal IgG2A and IgG1 antibodies from mice are compared to determine whether the immune response, if any, is of the Th1- or Th2-type.

Another set of BALB/c mice are immunized with β-Gal as described above and sacrificed 24 hours later. Spleens are harvested from each mouse and splenocytes are isolated as described previously. The splenocytes are added to microtiter wells pre-coated with anti-CD-3 antibody. (The anti-CD-3 antibody stimulates T cells through the T cell receptor complex.) The splenocytes are cultured in RPMI 1640 with 10% FBS at $4 \times 10^5$ cells/well and the supernatants sampled at 24, 48, and 72 hours of culture. Cytokine production by the splenocytes is determined with ELISA tests as described above. Relatively high levels of IFN-γ and IL-12 and relatively low levels of IL-4 would be expected with a Th1-type immune response. Relatively low levels of IFN-γ and IL-12 and relatively high levels of IL-4 would be expected with a Th2-type immune response. CTL activity of the splenocytes is determined.

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

I claim:

1. An immunomodulatory polynucleotide comprising an immunostimulatory sequence (ISS) comprising 5'-purine-purine-mC-G-pyrimidine-pyrimidine-3', wherein mC is a cytosine modified at position C-5 with a halogen.

2. An immunomodulatory polynucleotide of claim 1, wherein the ISS comprises the sequence 5'-purine-purine-mC-G-pyrimidine-pyrimidine-C-G-3'.

3. An immunomodulatory polynucleotide of claim 1, wherein the ISS comprises the sequence 5'-purine-purine-mC-G-pyrimidine-pyrimidine-C-C-3'.

4. An immunomodulatory polynucleotide of claim 1, wherein the ISS comprises the sequence 5'-purine-purine-C-G-pyrimidine-pyrimidine-mC-G-3'.

5. An immunomodulatory polynucleotide of claim 4, wherein the ISS comprises a sequence selected from the group consisting of AACGTTmCG and GACGTTmCG.

6. An immunomodulatory polynucleotide of claim 1, wherein the ISS comprises a sequence selected-from the group consisting of AAmCGTT, GAmCGTT, AAmCGTTCC, AAmCGTTCG, GAmCGTTCC, GAmCGTTCG, AAmCGTTmCG and GAmCGTTmCG.

7. An immunomodulatory polynucleotide of claim 1, wherein the ISS comprises a uracil.

8. An immunomodulatory polynucleotide of claim 7, wherein the ISS comprises a sequence selected from the group consisting of AAmCGUU, AAmCGUT, AAmCGTU, GAmCGUU, GAmCGUT, GAmCGTU, AAmCGUUCC, AAmCGUTCC, AAmCGTUCC, AAmCGUUCG, AAmCGUTCG, AAmCGTUCG, GAmCGUUCC, GAmCGUTCC, GAmCGTUCC, GAmCGUUCG, GAmCGUTCG, GAmCGTUCG, AAmCGUUmCG, AAmCGUTmCG, AAmCGTUmCG, GAmCGUUmCG, GAmCGUTmCG and GAmCGTUmCG.

9. An immunomodulatory polynucleotide according to any one of claims 3, 6 or 8, wherein the ISS further comprises a second mC, wherein mC is a cytosine modified at position C-5 with a halogen.

10. An immunomodulatory polynucleotide of claim 1, wherein the ISS comprises the sequence 5'-purine-purine-mC-G-pyrimidine-pyrimidine-mC-G-3'.

11. An immunomodulatory polynucleotide of claim 10, wherein the ISS comprises a sequence selected from the group consisting of AAmCGTTmCG and GAmCGTTmCG.

12. An immunomodulatory polynucleotide according to any one of claims 1, 2, 3, 4 or 10, wherein the polynucleotide is greater than 15 nucleotides in length.

13. An immunomodulatory polynucleotide according to any one of claims 1, 2, 3, 4 or 10, wherein the polynucleotide is greater than 20 nucleotides in length.

14. A composition comprising an immunomodulatory polynucleotide according to any one of claims 1, 2, 3, 4 or 10 and an allergen.

15. A composition of claim 14, wherein the allergen is linked to the immunomodulatory polynucleotide.

16. A composition of claim 14, further comprising a pharmaceutically acceptable carrier.

17. An immunomodulatory polynucleotide according to any one of claims 1, 2, 3, 4 or 10 wherein the halogen is selected from fluorine, chlorine, bromine or iodine.

18. An immunomodulatory polynucleotide of claim 17, wherein the modified cytosine is a 5'-bromocytosine.

19. A composition comprising an immunomodulatory polynucleotide according to any one of claims 1, 2, 3, 4 or 10 and a pharmaceutically acceptable carrier.

20. A composition comprising an immunomodulatory polynucleotide according to any one of claims 1, 2, 3, 4 or 10 and an antigen.

21. A composition of claim 20, wherein the antigen is selected from the group consisting of polypeptides, glycoproteins, polysaccharides, and lipids.

22. A composition of claim 20, wherein the antigen is linked to the immunomodulatory polynucleotide.

23. A composition of claim 20, further comprising an adjuvant.

24. A composition of claim 20, further comprising a pharmaceutically acceptable carrier.

25. An immunomodulatory polynucleotide comprising the sequence SEQ ID NO:2.

26. A composition comprising an immunomodulatory polynucleotide according to claim 25 and a pharmaceutically acceptable carrier.

27. A composition comprising an immunomodulatory polynucleotide according to claim 25 and an antigen.

28. A composition of claim 27, wherein the antigen is linked to the immunomodulatory polynucleotide.

29. A composition of claim 27, further comprising a pharmaceutically acceptable carrier.

30. A composition comprising an immunomodulatory polynucleotide according to claim 25 and an allergen.

31. A composition of claim 30, wherein the allergen is linked to the immunomodulatory polynucleotide.

32. A composition of claim 30, further comprising a pharmaceutically acceptable carrier.

33. An immunomodulatory polynucleotide comprising the sequence SEQ ID NO:5.

34. A composition comprising an immunomodulatory polynucleotide according to claim 33 and a pharmaceutically acceptable carrier.

35. A composition comprising an immunomodulatory-polynucleotide according to claim 33 and an antigen.

36. A composition of claim 35, wherein the antigen is linked to the immunomodulatory polynucleotide.

37. A composition of claim 35, further comprising a pharmaceutically acceptable carrier.

38. A composition comprising an immunomodulatory polynucleotide according to claim 33 and an allergen.

39. A composition of claim 38, wherein the allergen is linked to the immunomodulatory polynucleotide.

40. A composition of claim 38, further comprising a pharmaceutically acceptable carrier.

41. An immunomodulatory polynucleotide comprising the sequence SEQ ID NO:6.

42. A composition comprising an immunomodulatory polynucleotide according to anyone of claims 1, 2, 3, 4, 10, 25, 33 or 41 and further comprising a facilitator selected from the group consisting of cytokines, chemokines, targeting protein ligand, a trans-activating factor, a peptide, and a peptide comprising a modified amino acid.

43. A composition comprising an immunomodulatory-polynucleotide according to claim 41 and a pharmaceutically acceptable carrier.

44. A composition comprising an immunomodulatory polynucleotide according to claim 41 and an antigen.

45. A composition of claim 44, wherein the antigen is linked to the immunomodulatory polynucleotide.

46. A composition of claim 44, further comprising a pharmaceutically acceptable carrier.

47. An immunomodulatory polynucleotide according to any one of claims 1, 2, 3, 4, 10, 25, 33 or 41, wherein the polynucleotide stimulates production of a Th1-type cytokine.

48. A composition comprising an immunomodulatory polynucleotide according to claim 41 and an allergen.

49. A composition of claim 48, wherein the allergen is linked to the immunomodulatory polynucleotide.

50. A composition of claim 48, further comprising a pharmaceutically acceptable carrier.

51. An immunomodulatory polynucleotide comprising an immunostimulatory sequence (ISS) comprising 5'-T-mC-G-3', wherein mC is a cytosine modified at position C-5 with a halogen.

52. An immunomodulatory polynucleotide of claim 51, wherein the halogen is fluorine, chlorine, bromine or iodine.

53. An immunomodulatory polynucleotide of claim 52, wherein the modified cytosine is a 5'-bromocytosine.

54. An immunomodulatory polynucleotide of claim 51, wherein the ISS further comprises a uracil.

55. A composition comprising an immunomodulatory polynucleotide according to claim 51 and a pharmaceutically acceptable carrier.

56. A composition comprising an immunomodulatory polynucleotide according to claim 51 and an antigen.

57. A composition of claim 56, wherein the antigen is selected from the group consisting of polypeptides, glycoproteins, polysaccharides, and lipids.

58. A composition of claim 56, wherein the antigen is linked to the immunomodulatory polynucleotide.

59. A composition of claim 56, further comprising an adjuvant.

60. A composition of claim 56, further comprising a pharmaceutically acceptable carrier.

61. A composition comprising an immunomodulatory polynucleotide according to claim 51, and further comprising a facilitator selected from the group consisting of cytokines, chemokines, targeting protein ligand, a trans-activating factor, a peptide, and a peptide comprising a modified amino acid.

62. An immunomodulatory polynucleotide of claim 51, wherein the polynucleotide is greater than 15 nucleotides in length.

63. An immunomodulatory polynucleotide of claim 51, wherein the polynucleotide is greater than 20 nucleotides in length.

64. An immunomodulatory polynucleotide of claim 51, wherein the polynucleotide stimulates production of a Th1-type cytokine.

65. A composition comprising an immunomodulatory polynucleotide according to claim 51 and an allergen.

66. A composition of claim 65, wherein the allergen is linked to the immunomodulatory polynucleotide.

67. A composition of claim 65, further comprising a pharmaceutically acceptable carrier.

* * * * *